United States Patent
Shen et al.

(10) Patent No.: US 11,075,084 B2
(45) Date of Patent: Jul. 27, 2021

(54) CHEMISTRIES FOR ETCHING MULTI-STACKED LAYERS

(71) Applicant: L'Air Liquide, Societe Anonyme pour l'Etude et l'Exploitation des Procedes Georges Claude, Paris (FR)

(72) Inventors: Peng Shen, Ibaraki (JP); Keiichiro Urabe, Ibaraki (JP); Jiro Yokota, Ibaraki (JP); Nicolas Gosset, Grenoble (FR)

(73) Assignee: L'Air Liquide, Société Anonyme pour l'Etude et l'Exploitation des Procédés Georges Claude, Paris (FR)

( * ) Notice: Subject to any disclaimer, the term of this patent is extended or adjusted under 35 U.S.C. 154(b) by 0 days.

(21) Appl. No.: 15/692,247

(22) Filed: Aug. 31, 2017

(65) Prior Publication Data

US 2017/0365487 A1   Dec. 21, 2017

(51) Int. Cl.
    *H01L 21/311* (2006.01)
    *H01L 21/306* (2006.01)
    (Continued)

(52) U.S. Cl.
    CPC ........ *H01L 21/30604* (2013.01); *C07C 19/08* (2013.01); *C23C 16/24* (2013.01);
    (Continued)

(58) Field of Classification Search
    CPC ............. H01L 21/30604; H01L 21/311; H01L 21/31105; H01L 21/31111; H01L 21/31116
    See application file for complete search history.

(56) References Cited

U.S. PATENT DOCUMENTS

| 5,176,790 A | 1/1993 | Arleo et al. |
| 6,015,761 A | 1/2000 | Merry et al. |

(Continued)

FOREIGN PATENT DOCUMENTS

| JP | 2008 300616 | 12/2008 |
| WO | WO 2014 070838 | 5/2014 |
| WO | WO 2017 026197 | 2/2017 |

OTHER PUBLICATIONS

Bogart et al, Mask charging and profile evolution during chlorine plasma etching of silicon, J. Vac. Sci. Technol. A, 18(1), Jan./Feb. 2000, pp. 197-206.

(Continued)

*Primary Examiner* — Jae Lee
(74) *Attorney, Agent, or Firm* — Yan Jiang

(57) ABSTRACT

Methods for fabricating a 3D NAND flash memory are disclosed. The method includes the steps of forming a hardmask pattern on the hardmask layer, and using the hardmask pattern to form apertures in the alternating layers by selectively plasma etching the alternating layers versus the hardmask layer using a hydrofluorocarbon etching gas selected from the group consisting of 1,1,1,3,3,3-hexafluoropropane ($C_3H_2F_6$), 1,1,2,2,3,3-hexafluoropropane (iso-$C_3H_2F_6$), 1,1,1,2,3,3,3-heptafluoropropane ($C_3HF_7$), and 1,1,1,2,2,3,3-heptafluoropropane (iso-$C_3HF_7$), wherein the first etching layer comprises a material different from that of the second etching layer.

20 Claims, 16 Drawing Sheets

(51) Int. Cl.

| | | |
|---|---|---|
| *C07C 19/08* | (2006.01) | |
| *C23C 16/24* | (2006.01) | |
| *C23C 16/26* | (2006.01) | |
| *C23C 16/34* | (2006.01) | |
| *C23C 16/40* | (2006.01) | |
| *C23C 16/56* | (2006.01) | |
| *H01L 27/11582* | (2017.01) | |
| *H01L 27/1157* | (2017.01) | |
| *H01L 21/02* | (2006.01) | |

(52) U.S. Cl.
CPC ............ *C23C 16/26* (2013.01); *C23C 16/345* (2013.01); *C23C 16/402* (2013.01); *C23C 16/56* (2013.01); *H01L 21/31116* (2013.01); *H01L 21/31144* (2013.01); *H01L 27/1157* (2013.01); *H01L 27/11582* (2013.01); *H01L 21/02019* (2013.01); *H01L 21/02115* (2013.01); *H01L 21/02123* (2013.01)

(56) References Cited

U.S. PATENT DOCUMENTS

| | | | |
|---|---|---|---|
| 6,074,959 A | 6/2000 | Wang et al. | |
| 6,120,697 A * | 9/2000 | Demmin | H01L 21/31116 252/79.1 |
| 6,183,655 B1 | 2/2001 | Wang et al. | |
| 6,387,287 B1 | 5/2002 | Hung et al. | |
| 6,428,716 B1 | 8/2002 | Demmin et al. | |
| 9,017,571 B2 | 4/2015 | Umezaki et al. | |
| 9,460,935 B2 | 10/2016 | Chung | |
| 2008/0041526 A1* | 2/2008 | Pass | H01L 21/67063 156/345.31 |
| 2009/0176375 A1* | 7/2009 | Benson | H01L 21/31116 438/719 |
| 2012/0261722 A1* | 10/2012 | Tang | H01L 27/101 257/202 |
| 2016/0218015 A1 | 7/2016 | Oomori et al. | |
| 2018/0204728 A1* | 7/2018 | Oomori | H01L 21/3065 |

OTHER PUBLICATIONS

Karecki et al, Use of Novel Hydrofluorocarbon and Iodofluorocarbon Chemistries for a High Aspect Ratio via Etch in a High Density Plasma Etch Tool, J. Electrochem. Soc., vol. 145, No. 12, Dec. 1998, pp. 4305-4312.

Kwon et al, Infinite Etch Selectivity during Etching of SiON with an Extreme Ultraviolet Resist Pattern in Dual-Frequency Capacitively Coupled Plasmas, J. Electrochem. Soc., vol. 157, No. 1, (2010) pp. D21-D28.

Kwon et al, Ultrahigh Selective Etching of SiO2 Using an Amorphous Carbon Mask in Dual-Frequency Capacitively Coupled $C_4F_8$/$CH_2F_2$/O2/Ar Plasmas, J. Electrochem. Soc., vol. 157, No. 3, (2010) pp. D135-D141.

Miyake et al, Characterization of Polymer Layer Formation During $SiO_2$—SiN Etching by Fluoro/Hydrofluorcarbon Plasmas, Japanese Journal of Applied Physics, vol. 53, (2014) pp. 03DD02-1-03DD02-6.

International Search Report and Written Opinion for corresponding PCT/IB2018/000954, dated Dec. 11, 2018.

* cited by examiner

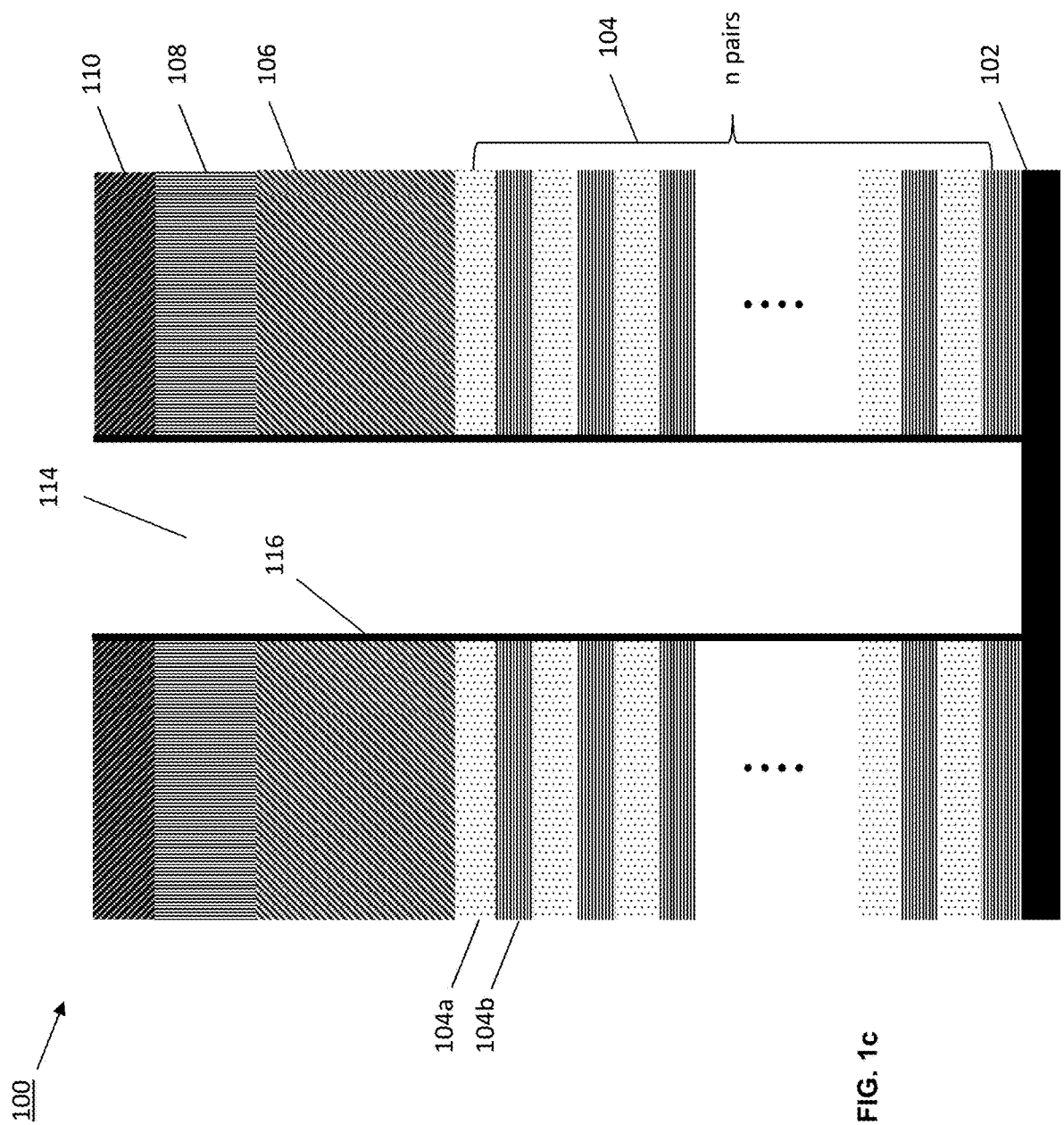

CHEMISTRIES FOR ETCHING MULTI-STACKED LAYERS

TECHNICAL FIELD

The present concept relates to a method for fabricating a semiconductor device and, more particularly, to a method for fabricating 3D NAND architectures using an etching gas capable of etching multi-stacked layers.

BACKGROUND

Silicon oxide and silicon nitride (SiO/SiN) are important compositions for tunnel and charge trapping in NAND type flash memory. Etching is applied to remove silicon oxide and silicon nitride films from semiconductor substrates in memory applications. For memory applications, such as 3D NAND (e.g., see US 2011/0180941), etching of stacks of multiple SiO/SiN layers is critical. The challenge of etching vertical NAND memory (e.g., 3D NAND) is how to etch oxide and nitride layers with a similar etch rate as high as possible. Furthermore, the etched structure should have a straight vertical profile (high aspect ratio) without bowing and low line edge roughness (LER).

Traditional etch chemistries may not be able to provide a feature, such as a hole or trench, having an aspect ratio higher than 20:1. A high aspect ratio (e.g., >20:1) is necessary in the newer applications (e.g., 3D NAND), at least due to insufficient etch resistant polymer deposition on sidewalls during the plasma etching processes. Traditional etch gases include octafluorocyclobutane ($cC_4F_8$), hexafluoro-1,3-butane ($C_4F_6$), tetrafluoromethane $CF_4$, difluoromethane $CH_2F_2$, fluoromethane $CH_3F$, and/or fluoroform $CHF_3$. These hydrofluorocarbon etching gases may produce sidewall polymers —$C_xF_y$—, where x ranges from 0.01 to 1 and y ranges from 0.01 to 4. These sidewall polymers may be susceptible to etching. See Standaert et al (J. Vac. Sci. Technol. A, 22, 53, 2004). It is well known in the art that selectivity and polymer deposition rate increases as the ratio of C:F increases (i.e., $C_4F_6$>$C_4F_8$>$CF_4$) in the hydrofluorocarbons. See, e.g., U.S. Pat. No. 6,387,287 to Hung et al. As a result, the etched patterns may not be straight vertical and the etch structure may show bowing, change in dimensions, pattern collapse and/or increased roughness with the traditional etch chemistries. Bowing may result from ion deflection in very narrow etched spaces leading to bowing for the etch structures. See Bogart et al, J. Vac. Sci. Technol A, 18, 197 (2000). It is important to minimize bowing to achieve the etching profile with high aspect ratio (i.e., up to 200:1) needed for current applications (e.g., contact etch or 3D NAND).

It is challenging to find an etch gas that has similar high etch rates of $SiO_2$ and SiN in terms of getting a smooth sidewall of high aspect ratio etching structures in 3D NAND applications.

In 3D NAND applications, a stack of alternating layers of SiO layers and SiN layers are, for example, formed on a substrate and semiconductor structures, such as, contact holes, staircase contacts, etc., are etched through the alternating layers of SiO layers and SiN layers. Attempts to etch SiO and/or SiN layers using hydrofluorocarbons as etching gas have been performed.

Anderson et al. (WO2014/070838A) disclose a method for etching silicon containing layers with $C_4$ hydrofluorocarbons.

Umezaki et al. (U.S. Pat. No. 9,017,571) disclose using 1,3,3,3-tetrafluoropropene (trans- and cis-) and additive gas for etching silicon material, such as, silicon dioxide, silicon nitride, polycrystalline silicon, amorphous silicon and silicon carbide.

Wang et al. (U.S. Pat. No. 6,183,655) disclose using fluoropropylene and hydrofluorocarbon for etching $SiO_2$ with high selectivity (at least 20:1) to other non-oxide layer (e.g., SiN layer). The fluoropropylene and hydrofluorocarbon include 1,1,1,2,3,3,3-$C_3H_2F_6$ and 1,1,2,2,3,3,3-$C_3HF_7$.

Merry et al. (U.S. Pat. No. 6,015,761) disclose using hydrofluorocarbons to etch dielectric layer comprising silicon dioxide, undoped silicate glass, phophosilicate glass (PSG), borophosphosilicate glass (BPSG), silicon nitride, with microwave-activated plasma source. $C_3H_2F_6$ is listed in the examples of the fluorocarbon gas, but no any etching Examples using $C_3H_2F_6$ has been disclosed.

Arleo et al. (U.S. Pat. No. 5,176,790) disclose forming one or more vias through an insulation layer by plasma etching to an underlying metal layer. The etching gas includes non-cyclic 3-6 carbon fluorinated hydrocarbons $C_3H_2F_6$ and $C_3HF_7$, but no etching examples show etching with $C_3H_2F_6$ and $C_3HF_7$. The insulation materials comprise a deposited silicon oxide, a silicon nitride compound or a silicon oxynitride compound formed over the metal layer.

Chung et al. (U.S. Pat. No. 9,460,935) disclose a method for fabricating a semiconductor device. The method comprises forming a first etching layer and a second etching layer stacked on a substrate, and forming a recess region by etching the first and second etching layers under plasma generated from an etching gas including a compound. The compound comprises at least one of 1,1,1,2,3,3-hexafluoropropane, 2,2,2-trifluoroethane-1-thiol, 1,1,1,3,3-pentafluoropropane, 1,1,2,2,3-pentafluoropropane and 1,1,2,2-tetrafluoro-1-iodoethane, 2,3,3,3-tetrafluoropropene and 1,1-difluoroethene.

Demmin et al. (U.S. Pat. Nos. 6,120,697 and 6,428,716) disclose a method of etching with at least an etchant compound having the formula $C_xH_yF_z$ wherein: x=3, 4 or 5; 2x≥z≥y; and y+z=2x+2; and significant selectivities of $SiO_2$ over Si and $SiO_2$ over $Si_3N_4$ have been achieved by varying operating parameters such as pressure, bias, and power. In addition, the etching process is performed under conditions such that the etch ratios of $SiO_2$ over Si and/or $SiO_2$ over $Si_3N_4$ are no less than about 2:1.

Kwon et al. disclose hydrofluorocarbon ($CH_2F_2$) was used for etching of SiON (Kwon et al., "Infinite Etch Selectivity during Etching of SiON with an Extreme Ultraviolet Resist Pattern in Dual-Frequency Capacitively Coupled Plasmas", Journal of the Electrochemical Soc. (2010) 157, D21-D28).

Karecki et al. discloses using hydrofluorocarbon for high aspect ratio $SiO_2$ etching (Karecki et al., "Use of Novel Hydrofluorocarbon and Iodofluorocarbon Chemistries for a High Aspect Ratio Via Etch in a High Densily Plasma Etch Tool", Journal of the Electrochemical Soc. (1998) 145, 4305-4312).

There is still a lack of etching a plurality of alternating layers of SiO and SiN layers in a 3D NAND application using a nontraditional hydrofluorocarbon etching gas. Although there are numbers of prior arts for $SiO_2$ etching with high selectivity to SiN, for certain applications, such as etching of multi-layered 3D NAND memory, it is important to have an etching gas which can etch both $SiO_2$ and SiN layers (or both $SiO_2$ and p-Si layers) without selectivity. In another word, it is a challenge to find an etch gas that has similar high etch rates of $SiO_2$ and SiN in terms of getting a smooth sidewall of high aspect ratio holes in 3D NAND memory.

Thus, a need remains for finding an etching gas that is able to etch SiO/SiN layers, while maintaining similar high etch rate of SiO/SiN.

SUMMARY

Disclosed are methods for fabricating a 3D NAND flash memory having alternating layers of a first etching layer and a second etching layer on a substrate and a hardmask layer on the alternating layers. The disclosed methods include the steps of forming a hardmask pattern on the hardmask layer and using the hardmask pattern to form apertures in the alternating layers by selectively plasma etching the alternating layers versus the hardmask layer using a hydrofluorocarbon etching gas selected from the group consisting of 1,1,1,3,3,3-hexafluoropropane ($C_3H_2F_6$), 1,1,2,2,3,3-hexafluoropropane (iso-$C_3H_2F_6$), 1,1,1,2,3,3,3-heptafluoropropane ($C_3HF_7$), and 1,1,1,2,2,3,3-heptafluoropropane (iso-$C_3HF_7$), wherein the first etching layer comprises a material different from that of the second etching layer. The disclosed methods may include one or more of the following aspects:
- the hardmask layer being selected from the group consisting of CVD or spin on deposited layer of amorphous carbon or doped carbon, silicon-containing spin on mask, and carbon-containing spin on mask;
- the hardmask layer being an amorphous carbon (a-C) layer;
- the hardmask layer being a doped carbon layer;
- the hardmask layer being a silicon-containing spin on mask layer;
- the hardmask layer being a carbon-containing spin on mask layer;
- depositing alternating layers comprising depositing the first etching layer on the substrate, depositing the second etching layer on the first etching layer, depositing another first etching layer on the second etching layer, and alternately and repeatedly depositing first and second etching layers to form a stacking structure, wherein the stacking structure comprises a plurality pairs of the first and second etching layers on the substrate;
- the alternating layers comprising a layer of silicon oxide, silicon nitride, SiOCH, SiON, $Si_aO_bC_cN_dH_e$ (where a>1; b, c, d and e≥0) or combinations thereof;
- the alternating layers comprising oxygen atoms, nitrogen atoms, carbon atoms, hydrogen atoms or combinations thereof the alternating layers being a silicon containing film;
- the alternating layers comprising a layer of silicon oxide and a layer of silicon nitride;
- the alternating layers comprising alternating layers of silicon oxide and silicon nitride;
- the alternating layers being alternating layers of silicon oxide and silicon nitride;
- the first etching layer comprising a silicon oxide layer;
- the first etching layer comprising a silicon nitride layer;
- the second etching layer comprising a silicon oxide layer;
- the second etching layer comprising a silicon nitride layer;
- the alternating layers being selectively etched from the hardmask layer;
- the alternating layers being selectively etched from an a-C layer;
- the alternating layers being selectively etched from a doped carbon layer;
- the alternating layers being selectively etched from a silicon-containing spin on hardmask layer;
- the alternating layers being selectively etched from a carbon-containing spin on hardmask layer;
- the alternating layers of silicon oxide and silicon nitride being selectively etched from the hardmask layer;
- the alternating layers of silicon oxide and silicon nitride being selectively etched from an a-C layer;
- the alternating layers of silicon oxide and silicon nitride being selectively etched from a doped carbon layer;
- the alternating layers of silicon oxide and silicon nitride being selectively etched from a silicon-containing spin on hardmask layer;
- the alternating layers of silicon oxide and silicon nitride being selectively etched from a carbon-containing spin on hardmask layer;
- the silicon oxide layer being selectively etched from the hardmask layer;
- the silicon oxide layer being selectively etched from an a-C layer;
- the silicon oxide layer being selectively etched from a doped carbon layer;
- the silicon oxide layer being selectively etched from a silicon-containing spin on hardmask layer;
- the silicon oxide layer being selectively etched from a carbon-containing spin on hardmask layer;
- the silicon nitride layer being selectively etched from the hardmask layer;
- the silicon nitride layer being selectively etched from an a-C layer;
- the silicon nitride layer being selectively etched from a doped carbon layer;
- the silicon nitride layer being selectively etched from a silicon-containing spin on hardmask layer;
- the silicon nitride layer being selectively etched from a carbon-containing spin on hardmask layer;
- etching the alternating layers of the first and second etching layers by a single process with plasma generated from the hydrofluorocarbon etching gas;
- the hydrofluorocarbon etching gas etching both the first and second etching layers with high etch rates;
- the hydrofluorocarbon etching gas etching both the silicon oxide layer and the silicon nitride layer with high etch rates;
- the hydrofluorocarbon etching gas not selectively etching the silicon oxide layer and the silicon nitride layer with high etch rates;
- the selectivity of the hydrofluorocarbon etching gas etching both the first and second etching layers ranging from approximately 1:2 to approximately 2:1;
- the selectivity of the hydrofluorocarbon etching gas etching both the first and second etching layers being approximately 1:1;
- the selectivity of the hydrofluorocarbon etching gas etching both silicon oxide layer and the silicon nitride layer ranging from approximately 1:2 to approximately 2:1;
- the selectivity of the hydrofluorocarbon etching gas etching both silicon oxide layer and the silicon nitride layer being approximately 1:1;
- the hydrofluorocarbon etching gas containing at least one hydrogen;
- the hydrofluorocarbon etching gas being three carbon ($C_3$) hydrofluorocarbon ($C_3H_mF_n$, where m>0, n>0) compounds containing at least one hydrogen;
- the hydrofluorocarbon etching gas being a $C_3$ organofluorine compounds containing at least one hydrogen;

the hydrofluorocarbon etching gas being 1,1,1,3,3,3-hexafluoropropane ($C_3H_2F_6$);
the hydrofluorocarbon etching gas being 1,1,2,2,3,3-hexafluoropropane (iso-$C_3H_2F_6$);
the hydrofluorocarbon etching gas being 1,1,1,2,3,3,3-Heptafluoropropane ($C_3H_2F_7$);
the hydrofluorocarbon etching gas being 1,1,1,2,3,3-heptafluoropropane (iso-$C_3H_2F_7$);
the hydrofluorocarbon etching gas reacting with the silicon-containing film under plasma to form volatile by-products;
removing the by-products;
heating the hydrofluorocarbon etching gas for plasma etching to avoid condensation;
heating the hydrofluorocarbon etching gas for plasma etching to maintain a desired flow rate of the hydrofluorocarbon etching gas;
adding an oxygen containing gas to the hydrofluorocarbon etching gas;
the oxygen containing gas selected from the group consisting of $O_2$, $O_3$, CO, $CO_2$, NO, $NO_2$, $N_2O$, $SO_2$, COS, $H_2O$ and combination thereof;
the oxygen containing gas being $O_2$;
mixing the hydrofluorocarbon etching gas and the oxygen containing gas prior to forming the apertures to produce a mixture;
introducing the hydrofluorocarbon etching gas separately from the oxygen containing gas;
introducing the oxygen containing gas continuously and introducing the hydrofluorocarbon etching gas in pulses;
the oxygen containing gas comprising approximately 0.01% v/v to approximately 99.9% v/v of a total volume of the hydrofluorocarbon etching gas and oxygen containing gas;
the oxygen containing gas comprising approximately 0.01% v/v to approximately 10% v/v of a total volume of the hydrofluorocarbon etching gas and oxygen containing gas;
adding an inert gas to the hydrofluorocarbon etching gas;
not adding an inert gas to the hydrofluorocarbon etching gas;
the inert gas being selected from the group consisting of He, Ar, Xe, Kr, Ne and $N_2$;
the inert gas being Ar;
the inert gas being Xe;
the inert gas being Kr;
mixing the hydrofluorocarbon etching gas and the inert gas prior to forming the apertures to produce a mixture;
introducing the hydrofluorocarbon etching gas separately from the inert gas;
introducing the inert gas continuously and introducing the hydrofluorocarbon etching gas in pulses;
the inert gas comprising approximately 0.01% v/v to approximately 99.9% v/v of a total volume of the vapor of the hydrofluorocarbon etching compound and inert gas;
the inert gas comprising approximately 90% v/v to approximately 99% v/v of a total volume of the vapor of the hydrofluorocarbon etching compound and inert gas;
the substrate being a Si wafer;
the substrate being a crystalline silicon layer;
producing the apertures in the alternating layers having an aspect ratio between approximately 1:1 and approximately 50:1;
producing the apertures in the alternating layers having an aspect ratio between approximately 1:1 and approximately 200:1;
producing the apertures in the alternating layers having a bowing less than 5%;
producing the apertures in the alternating layers having a bowing less than 2%;
producing the apertures having a diameter ranging from approximately 5 nm to approximately 200 nm;
producing the apertures having a diameter of approximately 100 nm;
producing the apertures having a diameter of approximately 50 nm;
producing the apertures;
the aperture being 3D NAND apertures;
the aperture being contact holes;
the aperture being 3D NAND contact holes;
the aperture being staircase contacts;
producing channel holes having an aspect ratio between approximately 1:1 and approximately 200:1;
producing the channel holes in the alternating layers having a bowing less than 5%;
producing the channel holes in the alternating layers having a bowing less than 2%;
producing channel holes having a diameter ranging from approximately 5 nm to approximately 200 nm;
producing channel holes having a diameter of approximately 100 nm;
producing channel holes having a diameter of approximately 40 nm;
producing contact holes having an aspect ratio between approximately 1:1 and approximately 200:1;
producing contact holes having a diameter ranging from approximately 5 nm to approximately 200 nm;
producing the contact holes in the alternating layers having a bowing less than 5%;
producing the contact holes in the alternating layers having a bowing less than 2%;
producing contact holes having a diameter of approximately 100 nm;
producing contact holes having a diameter of approximately 40 nm;
improving selectivity by adding a second etch gas to the hydrofluorocarbon etching gas;
the second etch gas being selected from the group consisting of $cC_4F_8$, $C_4F_8$, $C_4F_6$, $C_5F_8$, $CF_4$, $CH_3F$, $CF_3H$, $CH_2F_2$, COS, $Cs_2$, $CF_3I$, $C_2F_3I$, $C_2F_5I$, FNO, $SO_2$ and combinations thereof;
mixing the hydrofluorocarbon etching gas and the second etch gas prior to forming the apertures;
introducing the hydrofluorocarbon etching gas separately from the second etch gas;
adding approximately 0.01% v/v to approximately 99.99% v/v of the etch second gas to the hydrofluorocarbon etching gas;
activating the plasma by applying RF power;
activating the plasma by a RF power ranging from approximately 25 W to approximately 20,000 W;
etching pressure ranging from approximately 1 mTorr to approximately 10 Torr;
etching pressure being 30 mTorr;
introducing the hydrofluorocarbon etching gas at a flow rate ranging from approximately 0.1 sccm to approximately 1 slm;
maintaining the substrate at a temperature ranging from approximately −196° C. to approximately 500° C.;

maintaining the substrate at a temperature ranging from approximately −120° C. to approximately 300° C.;

maintaining the substrate at a temperature ranging from approximately −100° C. to approximately 50° C.;

maintaining the substrate at a temperature ranging from approximately −10° C. to approximately 40° C.; and measuring the hydrofluorocarbon etching gas under plasma by Quadrupole mass spectrometer, optical emission spectrometer, FTIR, or other radical/ion measurement tool.

Also disclosed are hydrofluorocarbon etching compounds comprising an organofluorine compound selected from the group consisting of 1,1,1,3,3,3-hexafluoropropane ($C_3H_2F_6$), 1,1,2,2,3,3-hexafluoropropane (iso-$C_3H_2F_6$), 1,1,1,2,3,3,3-Heptafluoropropane ($C_3HF_7$), and 1,1,1,2,2,3,3-heptafluoropropane (iso-$C_3HF_7$). The disclosed organofluorine etching compounds include one or more of the following aspects:

the organofluorine etching gas containing at least one hydrogen;

the organofluorine etching gas being three carbon ($C_3$) hydrofluorocarbon ($C_3H_mF_n$, where m>0, n>0) compounds containing at least one hydrogen;

the organofluorine etching gas being a $C_3$ organofluorine compound containing at least one hydrogen;

the organofluorine etching gas being $C_3H_2F_6$;

the organofluorine etching gas being iso-$C_3H_2F_6$;

the organofluorine etching gas being $C_3HF_7$;

the organofluorine etching gas being iso-$C_3HF_7$;

having a purity ranging from approximately 95% to approximately 99.999% by volume;

comprising between approximately 10 parts per trillion to approximately 5% by volume trace gas impurities;

the trace gas impurities comprising water;

the trace gas impurities comprising $CO_2$;

the trace gas impurities comprising $N_2$; and the organofluorine etching gas having a water content of less than 20 ppmw.

NOTATION AND NOMENCLATURE

Certain abbreviations, symbols, and terms are used throughout the following description and claims, and include:

As used herein, the indefinite article "a" or "an" means one or more.

As used herein, "about" or "around" or "approximately" in the text or in a claim means±10% of the value stated.

As used herein, the term "etch" or "etching" refers to a plasma etch process (i.e., a dry etch process) in which ion bombardment accelerates the chemical reaction in the vertical direction so that vertical sidewalls are formed along the edges of the masked features at right angles to the substrate (Manos and Flamm, Plasma Etching an Introduction, Academic Press, Inc. 1989 pp. 12-13). The etching process produces apertures, such as vias, trenches, channel holes, gate trenches, staircase contacts, capacitor holes, contact holes, etc., in the substrate.

The term "pattern etch" or "patterned etch" refers to etching a non-planar structure, such as a patterned hardmask layer on a stack of silicon-containing films.

The term "pattern wafer" or "wafer" refers to a wafer having a stack of silicon-containing films on a substrate and a patterned hardmask layer on a stack of silicon-containing films formed for pattern etch.

The term "mask" refers to a layer that resists etching. The hardmask layer may be located above the layer to be etched.

The term "etch stop" refers to a layer that resists etching located below the layer to be etched that protects layers underneath.

The term "aspect ratio" refers to a ratio of the height of a trench (or via) to the width of the trench (or the diameter of the via).

The term "bowing" refers to an aperture having a larger diameter than the patterned diameter, thereby forming a convex or outwardly rounded structure.

The term "selectivity" means the ratio of the etch rate of one material to the etch rate of another material. The term "selective etch" or "selectively etch" means to etch one material more than another material, or in other words to have a greater or less than 1:1 etch selectivity between two materials.

The term "contact holes" refers to holes made in the dielectric film that will be filled with conductive metal in order to connect electrodes such as gates, sources, and drains of transistors to metal wiring layers.

The term "staircase contacts" refers to the contact holes formed in a staircase-shaped stack of electrode layers.

The term "independently" when used in the context of describing R groups should be understood to denote that the subject R group is not only independently selected relative to other R groups bearing the same or different subscripts or superscripts, but is also independently selected relative to any additional species of that same R group. For example, in the formula $MR^1_x(NR^2R^3)_{(4-x)}$, where M is an atom, x is 2 or 3, the two or three $R^1$ groups may, but need not be identical to each other or to $R^2$ or to $R^3$. Further, it should be understood that unless specifically stated otherwise, values of R groups are independent of each other when used in different formulas.

Note that herein, the terms "film" and "layer" may be used interchangeably. Furthermore, one of ordinary skill in the art will recognize that the terms "film" or "layer" used herein refer to a thickness of some material laid on or spread over a surface and that the surface may range from as large as the entire wafer to as small as a trench or a line.

Note that herein, the terms "aperture", "via", "hole" and "trench" may be used interchangeably to refer to an opening formed in a semiconductor structure.

Note that herein, the terms "etching compound" and "etching gas" may be used interchangeably. It is understood that an etching compound may correspond to, or related to an etching gas, and that the etching gas may refer to the etching compound.

As used herein, the abbreviation "NAND" refers to a "Negative AND" or "Not AND" gate; the abbreviation "2D" refers to 2 dimensional gate structures on a planar substrate; the abbreviation "3D" refers to 3 dimensional or vertical gate structures, wherein the gate structures are stacked in the vertical direction.

The standard abbreviations of the elements from the periodic table of elements are used herein. It should be understood that elements may be referred to by these abbreviations (e.g., Si refers to silicon, N refers to nitrogen, O refers to oxygen, C refers to carbon, H refers to hydrogen, F refers to fluorine, etc.).

The unique CAS registry numbers (i.e., "CAS") assigned by the Chemical Abstract Service are provided to identify the specific molecules disclosed.

Please note that the silicon-containing films, such as SiN and SiO, are listed throughout the specification and claims without reference to their proper stoichoimetry. The silicon-containing films may include pure silicon (Si) layers, such as crystalline Si, polysilicon (p-Si or polycrystalline Si), or amorphous silicon; silicon nitride ($Si_kN_l$) layers; or silicon oxide ($Si_nO_m$) layers; or mixtures thereof, wherein k, l, m, and n, inclusively range from 0.1 to 6. Preferably, silicon nitride is $Si_kN_l$, where k and l each range from 0.5 to 1.5. More preferably silicon nitride is $Si_3N_4$. Herein, SiN in the following description may be used to represent $Si_kN_l$ containing layers. Preferably silicon oxide is $Si_nO_m$, where n ranges from 0.5 to 1.5 and m ranges from 1.5 to 3.5. More preferably, silicon oxide is $SiO_2$. Herein, SiO in the following description may be used to represent $Si_nO_m$ containing layers. The silicon-containing film could also be a silicon oxide based dielectric material such as organic based or silicon oxide based low-kdielectric materials such as the Black Diamond II or III material by Applied Materials, Inc. with a formula of SiOCH. Silicon-containing film may also include $Si_aO_bN_c$ where a, b, c range from 0.1 to 6. The silicon-containing films may also include dopants, such as B, C, P, As and/or Ge.

As used herein, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances.

"Comprising" in a claim is an open transitional term which means the subsequently identified claim elements are a nonexclusive listing i.e. anything else may be additionally included and remain within the scope of "comprising." "Comprising" is defined herein as necessarily encompassing the more limited transitional terms "consisting essentially of" and "consisting of"; "comprising" may therefore be replaced by "consisting essentially of" or "consisting of" and remain within the expressly defined scope of "comprising".

"Providing" in a claim is defined to mean furnishing, supplying, making available, or preparing something. The step may be performed by any actor in the absence of express language in the claim to the contrary.

Any and all ranges recited herein are inclusive of their endpoints (i.e., x=1 to 4 or x ranges from 1 to 4 includes x=1, x=4, and x=any number in between), irrespective of whether the term "inclusively" is used.

BRIEF DESCRIPTION OF THE DRAWINGS

For a further understanding of the nature and objects of the present invention, reference should be made to the following detailed description, taken in conjunction with the accompanying drawings, in which like elements are given the same or analogous reference numbers and wherein:

FIG. 1b is a cross-sectional side view of an exemplary aperture formed by plasma etching in the 3D NAND stack of FIG. 1a;

FIG. 1c is a cross-sectional side view of an exemplary aperture formed by plasma etching in the 3D NAND stack of FIG. 1a having a polymer layer deposited on the sidewall of the exemplary aperture;

DESCRIPTION OF PREFERRED EMBODIMENTS

Figure 1A:
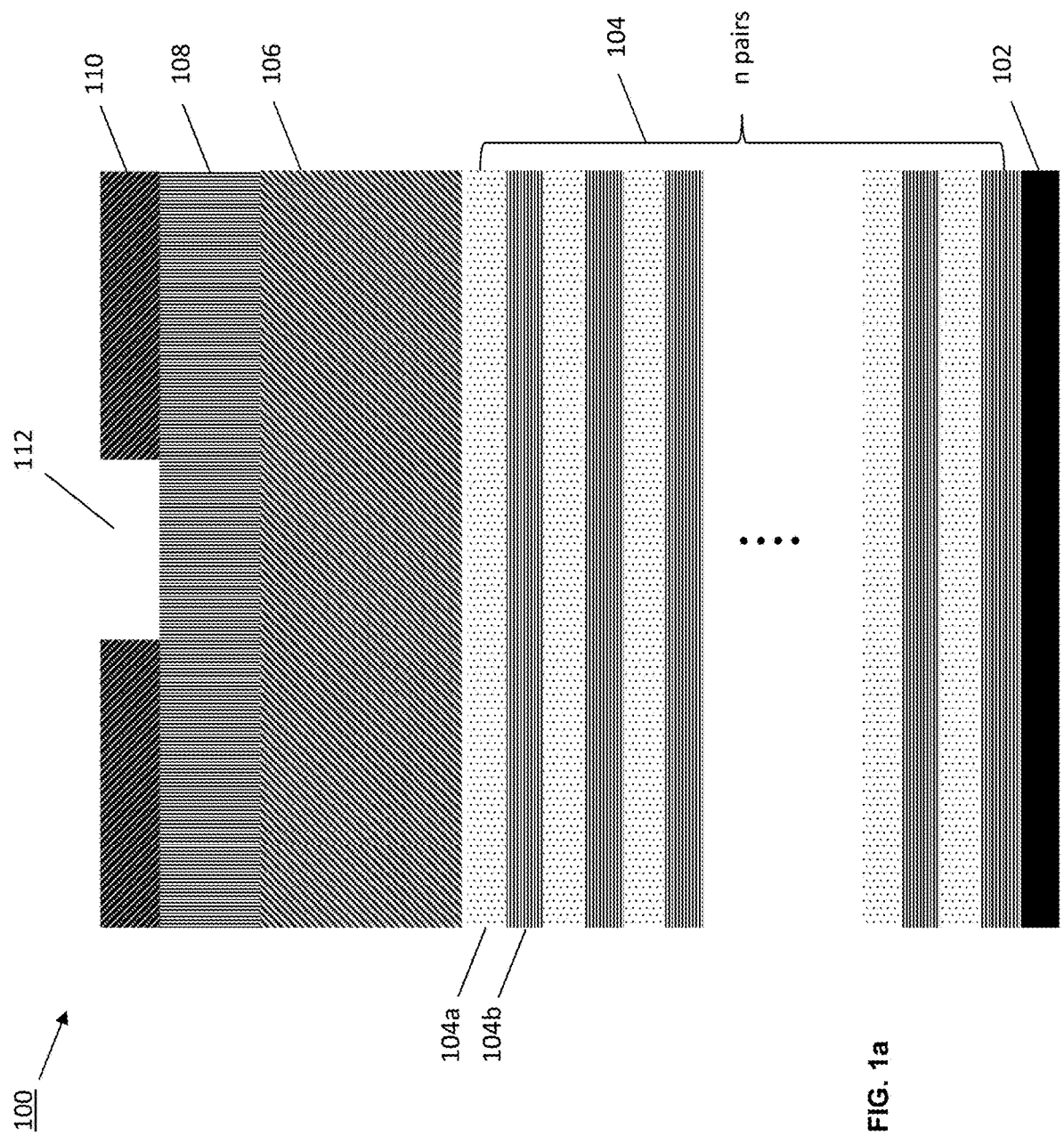
FIG. 1a is a cross-sectional side view of exemplary layers in a 3D NAND stack.

Disclosed are methods for fabricating a 3D NAND flash memory, more specifically, plasma etching silicon-containing films to produce semiconductor structures. The structures include, but are not limited to, SiO/SiN (ONON) channel hole, ONON trench, staircase contact holes, etc. The structures may have a top critical dimension (CD) of 5-200 nm. The disclosed methods produce the structures having high aspect ratio, less to no bowing and a decent amount of polymer deposition on the structures.

Here, the 3D NAND flash memory may have alternating layers of a first etching layer and a second etching layer on a substrate and a hardmask layer on the alternating layers. The disclosed methods may be suitable for producing any 3D NAND technology related semiconductor structures.

The disclosed methods include the steps of i) forming a hardmask pattern on the hardmask layer and ii) using the hardmask pattern to form apertures in the alternating layers by selectively plasma etching the alternating layers versus the hardmask layer using a hydrofluorocarbon etching gas. The hydrofluorocarbon etching gas is selected from the group consisting of 1,1,1,3,3,3-hexafluoropropane ($C_3H_2F_6$), 1,1,2,2,3,3-hexafluoropropane (iso-$C_3H_2F_6$), 1,1,1,2,3,3,3-heptafluoropropane ($C_3HF_7$), and 1,1,1,2,2,3,3-heptafluoropropane (iso-$C_3HF_7$). In the disclosed methods, the first etching layer comprises a material different from that of the second etching layer.

The disclosed methods may also include the steps of depositing the alternating layers of the first etching layer and the second etching layer on the substrate, and depositing the hardmask layer on the alternating layers.

The alternating layers of the first etching layer and the second etching layer are deposited on the substrate using deposition precursors suitable for chemical vapor deposition (CVD) or atomic layer deposition (ALD). The alternating layers are formed by depositing the first etching layer on the substrate, depositing the second etching layer on the first etching layer, depositing another first etching layer on the second etching layer, and alternately and repeatedly depositing first and second etching layers to form a stacking structure, wherein the stacking structure comprises a plurality of pairs of the first and second etching layers on the substrate.

More specifically, methods for depositing the alternating layers on the substrate include the following steps: i) the step of depositing the first etching layer on the substrate including: introducing a vapor of a first silicon containing precursor (for example, an organosilane containing oxygen) into a reactor having at least one substrate disposed therein, and at least part of the first silicon containing precursor is deposited onto the at least one substrate to form the first etching layer using a vapor deposition method, for example, plasma enhanced CVD or plasma enhanced ALD; ii) the step of depositing the second etching layer on the first etching layer including: introducing a vapor of a second silicon containing precursor (for example, an organosilane containing nitrogen) into the reactor, and at least part of the second silicon containing precursor is deposited onto the first etching layer to form the second etching layer using the vapor deposition method; iii) alternately and repeatedly depositing first and second etching layers to form a stacking structure, wherein the stacking structure comprises a plurality of pairs of the first and second etching layers on the substrate. (See U.S. Pat. No. 9,371,338 to Dussarrat, et al.). The plurality of pairs of the first and second etching layers may be 48 pairs, 96 pairs, 128 pairs, 264 pairs, or even more.

The alternating layers include at least one pair of the first and second etching layers. The alternating layers may include 96 pairs of the first etching layer and the second etching layer. Alternatively, the alternating layers may include 128 pairs of the first etching layer and the second etching layer. In another alternative, the alternating layers may include 264 pairs of the first etching layer and the second etching layer. In yet another alternative, the alternating layers may include more than 264 pairs of the first etching layer and the second etching layer.

The alternating layers may be a silicon containing film that includes a layer of silicon oxide, silicon nitride, SiOCN, SiON, $Si_aO_bH_cC_dN_e$, where a>0; b, c, d and e≥0, or combinations thereof. The silicon containing film may further include oxygen atoms, nitrogen atoms, carbon atoms, or combinations thereof.

The silicon containing film may be a SiO first etching layer and a SiN second etching layer, or vice versa. The silicon containing film contains at least one pair of the SiO and SiN layer. The silicon containing film may contain 96 pairs of the SiO and SiN layer. Alternatively, the silicon containing film may contain 128 pairs of the SiO and SiN layer. In another alternative, the silicon containing film may contain 264 pairs of the SiO and SiN layer. In yet another alternative, the silicon containing film may contain more than 264 pairs of the SiO and SiN layer.

The hardmask layer may be, but is not limited to, a CVD or spin on deposited layer of amorphous carbon (a-C) or doped carbon, silicon-containing spin on hardmask (SOH), carbon-containing spin on hardmask, photoresist, or combination thereof. The doped carbon may be Boron (B), Tungston (W), Titanium (Ti), Zirconium (Zr), Aluminum (Al) or combination doped carbon.

The hardmask layer is formed on the alternating layers by a CVD or spin on deposition method. The hardmask layer may be a spin on deposited layer of a-C. An anti-reflective layer formed by organic compounds, for example, polyamides and polysulfones, is deposited on the a-C layer and a photoresist layer is deposited on the anti-reflective layer. A photoresist layer pattern is formed by performing exposure (e.g., photolithographic process) and developing processes on the photoresist layer. An a-C layer pattern is formed by etching the anti-reflective layer and the a-C layer using the photoresist layer pattern as an etch mask. The a-C layer pattern forms a hardmask layer pattern. The alternating layers are then etched from the hardmask layer (i.e., the a-C layer) using the hardmask layer pattern as an etch mask to form a pattern containing apertures in the alternating layers (See US20130109198 to Dussarrat et al.). The apertures include contact holes or channel holes penetrating the alternating layers of the first etching layer and the second etching layer to expose the substrate.

The disclosed methods provide methods of etching the alternating layers of the first and second etching layers by a single process with plasma generated from the disclosed hydrofluorocarbon etching gases. The disclosed hydrofluorocarbon etching gases etch both the first and second etching layers with high etch rates, for example from 100 nm/min to 600 nm/min or even more. If the first etching layer is a silicon oxide layer and the second etching layer is a silicon nitride layer, or vice versa, the disclosed hydrofluorocarbon etching gases etch through the silicon oxide layer and the silicon nitride layer with high etch rates, e.g., from 100 nm/min to 600 nm/min or even more, and approximately 1:1 selectivity.

The disclosed hydrofluorocarbon etching gases are three carbon ($C_3$) hydrofluorocarbon ($C_3H_mF_n$, where m>0, n>0) compounds containing at least one hydrogen. The disclosed hydrofluorocarbon etching gases have boiling points ranging from −20° C. to room temperature (i.e. 25° C.) and suitable for using as etchants. These etching gases are not flammable, not toxic and commercially available. Their structure formula, CAS numbers, and boiling points are included in Table 1. One of ordinary skill in the art will recognize that the synthesis methods for these gases may be obtained using the CAS numbers provided.

TABLE 1

| Compounds | Formula | Structure | CAS # | Boiling point (° C.) |
|---|---|---|---|---|
| 1,1,1,3,3,3-hexafluoropropane | $C_3H_2F_6$ | 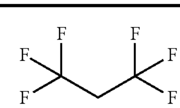 | 690-39-1 | −1.4 to −0.7 |

TABLE 1-continued

| Compounds | Formula | Structure | CAS # | Boiling point (° C.) |
|---|---|---|---|---|
| 1,1,2,2,3,3-hexafluoropropane | iso-C₃H₂F₆ | 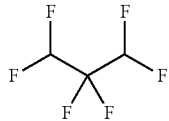 | 27070-61-7 | 5 |
| 1,1,1,2,3,3,3-Heptafluoropropane | C₃HF₇ | 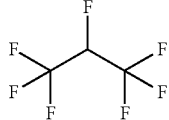 | 431-89-0 | −16 |
| 1,1,1,2,2,3,3-Heptafluoropropane | iso-C₃HF₇ | 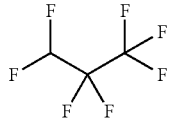 | 2252-84-8 | −16 |

The disclosed hydrofluorocarbon etching gases provide high to infinite selectivity to photoresist layers, mask layers, etch stop layers and device channel materials. The disclosed hydrofluorocarbon etching gases provide no selectivity to silicon-containing layers, such as SiO and SiN. The disclosed hydrofluorocarbon etching gases provide no profile distortion in high aspect ratio structures. For example, those have an aspect ratio ranging from 1:1 to 200:1 such as in 3D NAND applications. The disclosed hydrofluorocarbon etching gases provide similar etch rate of SiO₂ and SiN in terms of getting a smooth sidewall of high aspect ratio apertures or holes in 3D NAND applications. The resulting apertures may have an aspect ratio ranging from 1:1 to 50:1 in channel hole and contact hole etch applications, preferably an aspect ratio ranging from approximately 1:1 to approximately 200:1.

The disclosed hydrofluorocarbon etching gases also deposit a polymer passivation layer on the sidewalls of the apertures simultaneously while etching. By adding O₂ to the etch process, the thickness of the polymer passivation layer may be controlled to avoid sidewall profile deformation. The polymer passivation layer also provides smoother sidewalls, little to no bowing and little to no deformation at the bottom of the aperture in the 3D NAND stacks. If necessary, the polymer passivation layer may be easily removed or cleaned or polished by dry or wet etch chemistries well known in the art.

The disclosed hydrofluorocarbon etching gases provide approximately 1:1 selectivity between the alternating layers (e.g., silicon-containing films) in resulting patterned high aspect ratio structures. The disclosed hydrofluorocarbon etching gases provide infinite selectivity of mask materials to the alternating layers in the resulting patterned high aspect ratio structures. The disclosed hydrofluorocarbon etching gases also provide little to no damage to channel region in the resulting patterned high aspect ratio structures. Furthermore, the disclosed hydrofluorocarbon etching gases reduce bowing or provide little to no bowing in the resulting patterned high aspect ratio structures. In addition, the disclosed hydrofluorocarbon etching gases exhibit polymer deposition on the sidewall of the resulting high aspect ratio structures during the etching process. As a result, the disclosed processes produce little to no damage to channel region in the resulting high aspect ratio structures. The disclosed hydrofluorocarbon etching gases also etch through alternating layers of SiO/SiN in one process, resulting in a vertical etch profile. The selectivity of etching through the alternating layers of SiO/SiN ranges from approximately 1:2 to approximately 2:1, preferably around 1:1.

The disclosed hydrofluorocarbon etching gases may comprise greater than 95% v/v of the organofluorine compound, preferably greater than 99.99% v/v purity, and more preferably greater than 99.999% v/v purity. The disclosed hydrofluorocarbon etching gases contain less than 5% by volume trace gas impurities, with less than 150 ppm by volume of impurity gases, such as N₂ and/or H₂O and/or CO₂. Preferably, the water content in the plasma etching gas is less than 20 ppmw by weight. The purified product may be produced by distillation and/or passing the gas or liquid through a suitable adsorbent, such as a 4 A molecular sieve. Known standard purification techniques may also be used for removal of CO, CO₂, N₂, H₂O, HF, H₂S, SO₂, halides, and other hydrocarbons or hydrohalocarbons.

The disclosed hydrofluorocarbon etching gases contain less than 10% v/v, preferably less than 1% v/v, more preferably less than 0.1% v/v, and even more preferably less than 0.01% v/v of any of the isomers of the organofluorine compound, which may be purified by distillation of the gas or liquid to remove isomers and may provide better process repeatability.

Alternatively, the disclosed hydrofluorocarbon etching gases may contain between 5% v/v and 50% v/v of isomers of the organofluorine compound, particularly when the isomer mixture provides improved process parameters or if isolation of the target isomer is too difficult or expensive. For example, the disclosed hydrofluorocarbon etching gases may comprise between approximately 50% v/v and approximately 75% v/v 1,1,1,3,3,3-hexafluoropropane and between approximately 25% v/v and approximately 50% v/v 1,1,2,2,3,3-hexafluoropropane. The mixture of isomers may reduce the need for two or more gas lines to the reaction chamber.

The disclosed hydrofluorocarbon etching compounds are gaseous at room temperature and atmospheric pressure, and suitable for plasma etching semiconductor structures, such as, channel holes, staircase contacts, capacitor holes, contact holes, etc., in semiconductor devices, such as silicon-containing films. The disclosed hydrofluorocarbon etching gases are not only compatible with currently available mask materials but also compatible with the future generations of mask materials because the disclosed hydrofluorocarbon etching gases induce little to no damage on the mask. The disclosed hydrofluorocarbon etching compounds permit formation of good profiles in along with good profile of high aspect ratio structures. In other words, the disclosed hydrofluorocarbon etching gases may produce vertical etched patterns having minimal to no bowing, pattern collapse, or roughness. In order to achieve these properties, the disclosed hydrofluorocarbon etching gases may deposit an etch-resistant polymer layer during etching to help reduce the direct impact of the oxygen and fluorine radicals during the etching process. The disclosed hydrofluorocarbon etching gases may also reduce damage to crystalline Si channel structure during etching. As shown in the examples that follow, the disclosed hydrofluorocarbon etching gases are suitably volatile and stable during the etching process for delivery into the reactor/chamber.

If necessary, the container containing the disclosed etching compounds may be heated to a temperature that permits the disclosed etching compounds to have a sufficient vapor pressure for delivery into an etching tool or a reaction chamber. The container may be maintained at temperatures in the range of, for example, approximately 0° C. to approximately 150° C., preferably from approximately 25° C. to approximately 100° C., more preferably from approximately 25° C. to approximately 50° C. More preferably, the container is maintained at room temperature (approximately 25° C.). If necessary, the container containing the disclosed etching compounds and the gas lines delivering the disclosed etching compounds to an etching chamber or reaction chamber may be heated to avoid condensation due to cold points. Those skilled in the art would recognize that the temperature of the container and the gas lines may be adjusted in a known manner to control the amount of the disclosed etching gas delivered, such that the disclosed hydrofluorocarbon etching compounds maintain a predetermined flow rate to the reaction chamber without condensation. For example, the predetermined flow rate for the etching compounds shown in the following Examples 1-4 is 7.5 sccm. The disclosed hydrofluorocarbon etching gas may be introduced to the chamber at a flow rate ranging from approximately 0.1 sccm to approximately 1 slm. One of ordinary skill in the art will recognize that the flow rate may vary from tool to tool.

Material compatibility tests are important to determine if any of the disclosed hydrofluorocarbon etching gases will react with chamber materials and degrade the performance of the chamber with short term or long term use. Key materials involved in parts of the chamber, valves, etc. include stainless steel, aluminum, nickel, polychlorotrifluoroethene (PCTFE), polyvinylidene fluoride (PVDF), polytetrafluoroethylene (PTFE) and other metals and polymers. At times these materials are exposed to high temperatures, for example, higher than 20° C., and high pressures, for example, higher than 1 atm, which may enhance their degradation. The metrology methods may include visual inspection, weight measurement, measuring nanometer scale changes in scanning electron microscopy (SEM), tensile strength, hardness, etc.

The disclosed hydrofluorocarbon etching gases are used to plasma etch a multi-stacking layers (e.g., ONON) on a substrate. The disclosed plasma etching method is useful in the manufacture of semiconductor devices such as NAND or 3D NAND gates or flash memories. Due to the minimal sidewall damage incurred during the low k etch process, the disclosed hydrofluorocarbon etching gases are used for etching Si in 3D through silicon via (TSV) etch applications for interconnecting memory to logic on a substrate. Additionally, the disclosed hydrofluorocarbon etching gases may also be used for staircase etch such as ONON etch in 3D NAND.

The plasma etching method includes providing a reaction chamber having a substrate disposed therein. The reaction chamber may be any enclosure or chamber within a device in which etching methods take place such as, and without limitation, reactive ion etching (RIE), capacitively coupled plasma (CCP) with single or multiple frequency RF sources, inductively coupled plasma (ICP), or microwave plasma reactors, or other types of etching systems capable of selectively removing a portion of the multi-stacking layers (e.g., silicon-containing film) or generating active species. One of ordinary skill in the art will recognize that the different plasma reaction chamber designs provide different electron temperature control. Suitable commercially available plasma reaction chambers include but are not limited to the Applied Materials magnetically enhanced reactive ion etcher sold under the trademark eMAX™ or the Lam Research Dual CCP reactive ion etcher dielectric etch product family sold under the trademark 2300® Flex™. The RF power in such may be pulsed to control plasma properties and thereby improving the etch performance (selectivity and damage) further.

Alternatively, the plasma-treated reactant may be produced outside of the reaction chamber. The MKS Instruments' ASTRONi® reactive gas generator may be used to treat the reactant prior to passage into the reaction chamber. Operated at 2.45 GHz, 7 kW plasma power, and a pressure ranging from approximately 0.5 Torr to approximately 10 Torr, the reactant $O_2$ may be decomposed into two $O^-$ radicals. Preferably, the remote plasma may be generated with a power ranging from about 1 kW to about 10 kW, more preferably from about 2.5 kW to about 7.5 kW.

The reaction chamber may contain one or more than one substrate. For example, the reaction chamber may contain from 1 to 200 silicon wafers having from 25.4 mm to 450 mm diameters. The substrates may be any suitable substrates used in semiconductor, photovoltaic, flat panel or LCD-TFT device manufacturing. Examples of suitable substrates include wafers, such as silicon, silica, glass, or GaAs wafers. The wafer will have multiple films or layers on it from previous manufacturing steps, including multi-stacking layers (e.g., silicon-containing films). The layers may or may not be patterned. Examples of suitable layers include without limitation silicon (such as amorphous silicon, polysilicon (p-Si), crystalline silicon, any of which may further be p-doped or n-doped with B, C, P, As, and/or Ge), silica, silicon nitride, silicon oxide, silicon oxynitride, $Si_aO_bH_cC_dN_e$, (wherein a>0; b, c, d, e≥0), hardmask layer materials such as a-C, antireflective coatings, photoresist materials, tungsten, titanium nitride, tantalum nitride or combinations thereof, etch stop layer materials such as crystalline silicon, silicon carbide, SiCN or combinations thereof, device channel materials such crystalline silicon, epitaxial silicon, doped silicon, $Si_aO_bH_cC_dN_e$, (wherein a>0; b, c, d, e≥0) or combinations thereof. The silicon oxide layer may form a dielectric material, such as an organic based or silicon oxide based low-k dielectric material (e.g., a porous SiCOH film). An exemplary low-k dielectric material is sold by Applied Materials under the trade name Black Diamond II or III. Additionally, layers comprising tungsten or noble metals (e.g. platinum, palladium, rhodium or gold) may be used. Furthermore, examples of the silicon-containing films may be $Si_aO_bH_cC_dN_e$, (wherein a>0; b, c, d, e≥0).

Throughout the specification and claims, the wafer and any associated layers thereon are referred to as substrates.

The following are exemplary embodiments of the substrates (e.g., patterned wafers) on which the disclosed hydrofluorocarbon etching gases may be applied to etch.

In a disclosed embodiment, a substrate 100 may include a stack of multiple layers as shown in FIG. 1a. FIG. 1a is a cross-sectional side view of an exemplary 3D NAND stack. As shown, a stack of n pairs of alternative SiO/SiN or ONON layers 104 is located on top of a silicon wafer 102 (i.e., ONON or TCAT technology). 104a represents a SiO layer and 104b represents a SiN layer. Here n is integer. n may be 96. Alternatively, n may be 128, or even more. One of ordinary skill in the art will recognize the silicon wafer 102 may be replaced with tungsten (W) wafer. An a-C hardmask layer 106 is located on the top of the n pairs of SiO/SiN layers 104. The a-C hardmask layer 106 may contain C and H, as well as other elements, such as boron, nitrogen, etc., to improve etch resistance during SiO/SiN layer etch. An antireflective coating layer 108 is located on top of the a-C hardmask layer 106. A patterned photoresist layer 110 is located on top of the antireflective coating layer 108. The patterned photoresist layer 110 includes a plurality of patterned holes (one hole 112 is shown herein) that define a plurality of recess regions in the 3D NAND stack. The recess regions will be formed by etching the silicon containing film selectively versus a mask patterning layer under plasma generated from the disclosed hydrofluorocarbon etching gases. The hardmask layer may be CVD or spin on deposited layer of a-C, doped carbon, silicon-containing spin on mask, carbon-containing spin on mask, photoresist, etc. A SiON layer (not shown) may be present between the antireflective coating layer 108 and the a-C hardmask layer 106 to transfer pattern in photoresist layer 110 to the a-C layer 106. One of ordinary skill in the art will recognize that the stack of layers in the substrate 100 is provided for exemplary purposes only and that the disclosed hydrofluorocarbon etching gases may be used to etch other types of stacks of layers. Furthermore, one of ordinary skill in the art will recognize that the number of alternating SiO/SiN layers 104 in the stack of the substrate 100 may vary.

Figure 1B:
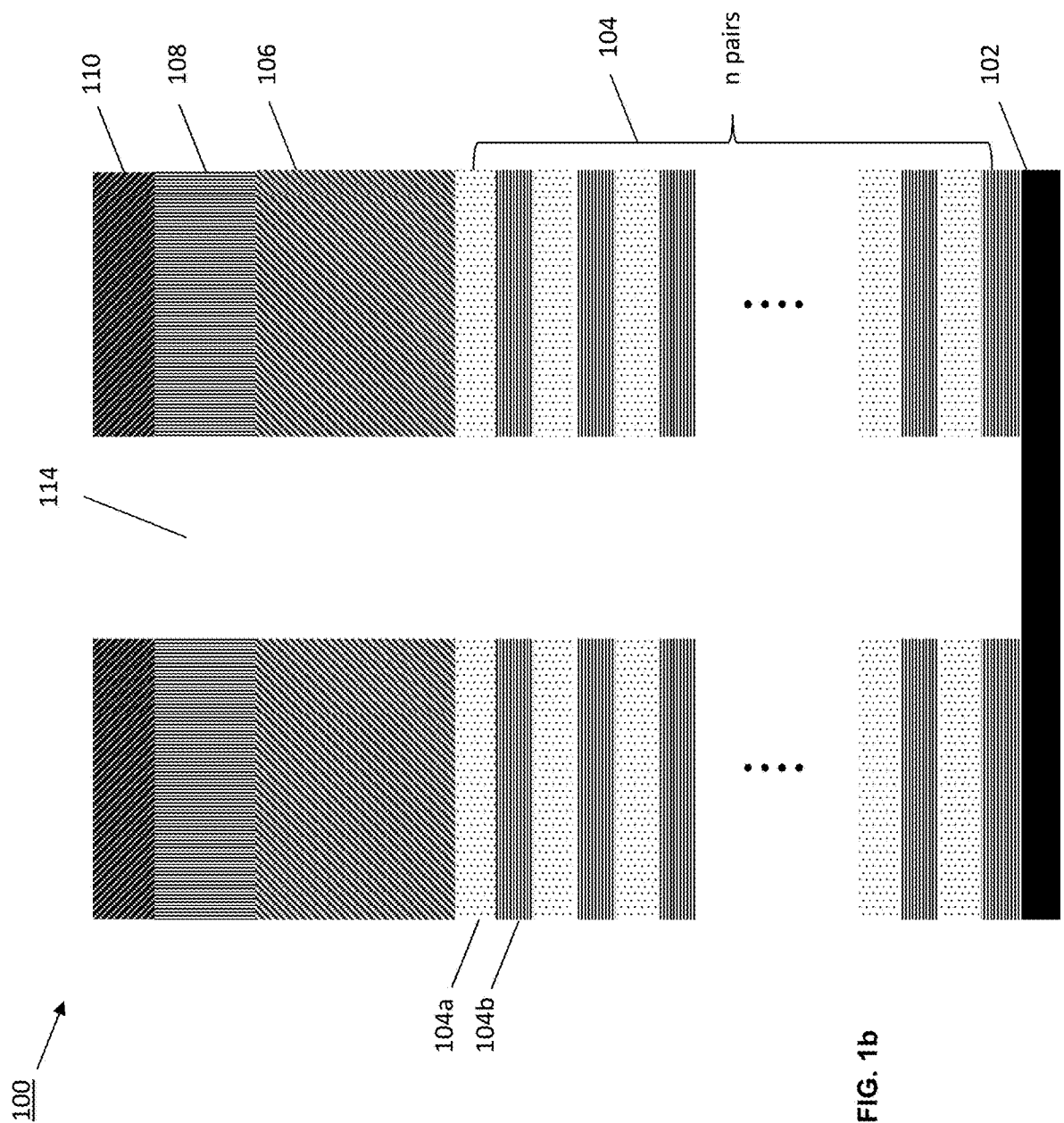

FIG. 1b is a cross-sectional side view of an exemplary aperture formed by plasma etching in the 3D NAND stack of FIG. 1a. The difference between FIG. 1b and FIG. 1a is in FIG. 1b via or aperture 114 is formed in substrate 100. Via 114 is formed by etching alternating SiO/SiN layers 104 using the disclosed hydrofluorocarbon etching compounds. Applicants believe via 114 may have an aspect ratio ranging from 1:1 to 50:1 in contact etch applications, preferably an aspect ratio ranging from approximately 1:1 to approximately 200:1 by plasma etching using the disclosed hydrofluorocarbon etching compounds. The disclosed hydrofluorocarbon etching gases are able to etch both $SiO_2$ and SiN layers in the stacked alternating SiO/SiN layers 104 with almost the same or close etch rates. That is, the stacked alternating SiO/SiN layer 104 is etched by a single etchant with a single process, rather than etching alternatively with alternative etchants to SiO and SiN, respectively. The disclosed hydrofluorocarbon etching gases have similar etch rates of $SiO_2$ and SiN (i.e., etching selectivity of $SiO_2$ to SiN is approximately 1:1, preferably, etching selectivity of $SiO_2$ to SiN ranging from approximately 1:2 to approximately 2:1) in terms of getting a smooth sidewall of high aspect ratio holes in 3D NAND memory applications.

FIG. 1c is a cross-sectional side view of an exemplary aperture formed by plasma etching in the 3D NAND stack of FIG. 1a having a polymer layer deposited on the sidewall of the exemplary aperture. The disclosed hydrofluorocarbon etching gases may produce fragments during the plasma process that are suitable for both anisotropically etching the silicon-containing films and depositing a polymer passivation layer on sidewalls of the structure being etched. The difference between FIG. 1c and FIG. 1a is in FIG. 1c while forming via 114 in substrate 100 by plasma etching using the disclosed hydrofluorocarbon etch gas, a polymer passivation layer 116 on the sidewalls of the via 114 is also formed simultaneously. By adding $O_2$ to the disclosed hydrofluorocarbon etch gas, the thickness of the polymer passivation layer 116 is under control thereby avoiding the sidewall profile deformation due to the polymer deposition. The polymer passivation layer 116 formed by the disclosed hydrofluorocarbon etch gas also provides smoother sidewall, little to no bowing and little deformation at the bottom of the via 114. The polymer passivation layer 116 may however be easily removed or cleaned by dry or wet etch chemistries well known in the art.

Figure 1D:
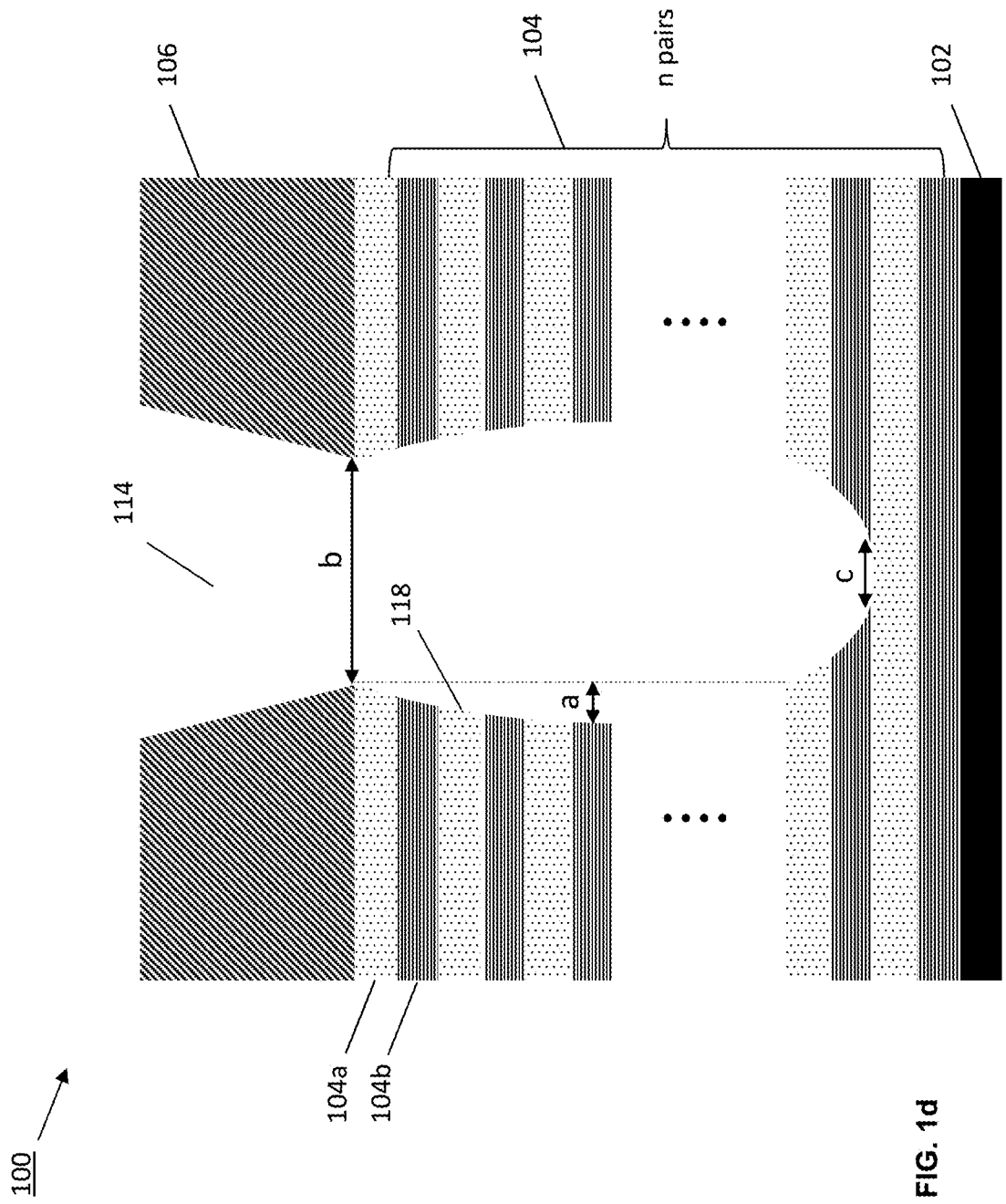
FIG. 1d is a cross-sectional side view of an exemplary aperture formed by plasma etching in the 3D NAND stack of FIG. 1a having sidewall bowing.

FIG. 1d is a cross-sectional side view of an exemplary aperture formed by plasma etching in the 3D NAND stack of FIG. 1a having sidewall bowing. As shown, in an actual etching process, the a-C hardmask patterned layer 106 has a tapered profile. The antireflective coating layer 108 and the patterned photoresist layer 110 are not shown. Sidewall necking (not shown) may occur in the a-C hardmask patterned layer 106 or around the aperture opening that may narrow the opening of the via 114. The sidewall necking is formed by redeposition of particles sputtered from the sloped sidewall of the mask pattern. The sidewall necking decreases the etch rates and the bottom diameter, which eventually affects the contact resistance. Thus, sidewall necking should be reduced or avoided around the aperture opening (i.e., around ONON opening of the via 114) in the etching process. The sidewall 118 of the etched structure with a polymer layer deposition (not shown) is bowed and not vertically straight, which lowers the quality of high-aspect-ratio etch hole. It is known the sidewall bowing or barreling results from the lateral etching by bombardments of deviated ions, and it is accelerated by the lack of a sufficient protective layer on the sidewall of high aspect-ratio etch holes. The bowed profile is a bottleneck to the scale-down of the 3D NAND architecture, resulting in a reduced process margin between the etch holes. In FIG. 1d, "a" represents maximum sidewall etching, "b" represents ONON opening line width and "c" represents bottom line width of the exemplary aperture formed by plasma etching. Bowing can be determined by the ratio of the sidewall etching by the following equation: bowing=(a/b)×100. Line width bias can be defined by the difference between the opening line width and bottom line width, i.e., line width bias=b−c. Line width bias represents etch stop due to shrinking bottom line width. The ideal etch profile has no bowing, that is, bowing=0. That is, the maximum line width is equal to the ONON opening line width for the structure being etched. In an actual practice, a bowing of nearly 0 is always desired. Preferably, bowing is less than 5% (or bowing is 0-5%). More preferably, bowing is less than 2% (or bowing is 0-2%).

The bowing of the sidewall 118 may be reduced by using the disclosed hydrofluorocarbon etching gases. Applicants believe that the disclosed hydrofluorocarbon gases reduce or eliminate the bowing of the sidewall 118 of the etch holes.

One of ordinary skill in the art will recognize that the stack and geometry of layers in FIG. 1a to FIG. 1d are provided for exemplary purposes only and that the disclosed hydrofluorocarbon etching gases may be used to etch other types of stacks of layers. Furthermore, one of ordinary skill in the art will recognize that the number of layers in the stack may vary (i.e., may include more or less than the layers depicted).

The disclosed hydrofluorocarbon etching gas is introduced into the reaction chamber containing the substrate and the alternating layers of the first etching layer and the second etching layer. If necessary, the container containing the disclosed etching gases and the gas lines delivering the disclosed hydrofluorocarbon etching gases to the reaction chamber may be heated to avoid condensation in the delivery gas lines due to cold points. The temperature of the container and the gas line may be adjusted in a known manner to control the amount of the disclosed hydrofluorocarbon etching gases delivered, such that the disclosed hydrofluorocarbon etching gas maintain a desired flow rate to the reaction chamber without condensation. The disclosed hydrofluorocarbon etching gas may be introduced to the chamber at a flow rate ranging from approximately 0.1 sccm to approximately 1 slm. For example, for a 200 mm wafer size, the disclosed hydrofluorocarbon etching gas may be introduced to the chamber at a flow rate ranging from approximately 5 sccm to approximately 50 sccm. Alternatively, for a 450 mm wafer size, the disclosed hydrofluorocarbon etching gas may be introduced to the chamber at a flow rate ranging from approximately 25 sccm to approximately 250 sccm. One of ordinary skill in the art will recognize that the flow rate may vary from tool to tool.

An oxygen-containing gas is introduced into the reaction chamber in order to eliminate high polymer deposition or reduce the thickness of the high polymer deposition. The oxygen-containing gas include, without limitation, oxidizers such as, $O_2$, $O_3$, CO, $CO_2$, NO, $NO_2$, $N_2O$, $SO_2$, COS, $H_2O$ and combinations thereof. It is known that addition of oxygen or oxygen containing gases to the plasma chemistry increases F/C ratio of plasma species and reduces polymer formation (See, e.g., U.S. Pat. No. 6,387,287 to Hung et al.). The disclosed etching gases and the oxygen containing gas may be mixed together prior to introducing into the reaction chamber.

Alternatively, the oxygen-containing gas is introduced continuously into the chamber and the disclosed hydrofluorocarbon etching gas introduced into the chamber in pulses. The oxygen-containing gas comprise between approximately 0.01% v/v to approximately 99.99% v/v of the mixture introduced into the chamber (with 99.99% v/v representing introduction of almost pure oxidizer for the continuous introduction alternative).

A second etch gas may be added to the disclosed hydrofluorocarbon etch gases. The second etch gas is selected from the group consisting of $cC_4F_8$, $C_4F_8$, $C_4F_6$, $C_5F_8$, $CF_4$, $CH_3F$, $CF_3H$, $CH_2F_2$, COS, $CS_2$, $CF_3I$, $C_2F_3I$, $C_2F_5I$, FNO, $SO_2$ and combination thereof.

The disclosed hydrofluorocarbon etching gas may be supplied either in neat form or in a blend with an inert gas. The inert gas may optionally be introduced into the reaction chamber and may help to sustain the plasma. The inert gas may be He, Ar, Xe, Kr, Ne, $N_2$ or combinations thereof. Preferably, the inert gas is Ar, Xe, Kr or combinations thereof. The disclosed hydrofluorocarbon etching gas and the inert gas may be mixed prior to introduction to the chamber, with the inert gas comprising between approximately 0.01% v/v and approximately 99.9% v/v of the resulting mixture. Alternatively, the inert gas may be introduced to the chamber continuously while the disclosed hydrofluorocarbon etching gas is introduced to the chamber in pulses. The disclosed hydrofluorocarbon etching gas may be present in varying concentrations in the blend with the inert gas.

The disclosed hydrofluorocarbon etching gas and inert gas are activated by plasma to produce an activated etching gas. The plasma decomposes the disclosed hydrofluorocarbon etching gas into radical form (i.e., the activated etching gas). The plasma may be generated by applying RF or DC power. The plasma may be generated with a RF power ranging from about 25 W to about 20,000 W. The plasma may be generated remotely or within the reactor itself. The plasma may be generated in dual CCP or ICP mode with RF applied at both electrodes. RF frequency of plasma may range from 200 KHz to 1 GHz. Different RF sources at different frequency may be coupled and applied at same electrode. Plasma RF pulsing may be further used to control molecule fragmentation and reaction at substrate. One of skill in the art will recognize methods and apparatus suitable for such plasma treatment.

Quadrupole mass spectrometer (QMS), optical emission spectrometer, FTIR, or other radical/ion measurement tools may measure the activated etching gas from the chamber exhaust to determine the types and numbers of species produced. If necessary, the flow rate of the etching gas and/or the inert gas may be adjusted to increase or decrease the number of radical species produced.

The disclosed hydrofluorocarbon etching gas may be mixed with other gases either prior to introduction into the reaction chamber or inside the reaction chamber. The disclosed hydrofluorocarbon etching gas and the other gases may be mixed prior to introduction to the chamber in order to provide a uniform concentration of the entering gas.

In another alternative, the disclosed hydrofluorocarbon gas may be introduced into the chamber independently of the other gases such as when two or more of the gases react.

In another alternative, the disclosed hydrofluorocarbon etching gas and the oxygen containing gas are the only two gases that are used during the etching process.

In another alternative, the disclosed hydrofluorocarbon etching gas, the oxygen containing gas and the inert gas are the only three gases that are used during the etching process.

The disclosed hydrofluorocarbon etching gas and the second etch gas may be mixed prior to introduction to the reaction chamber. The second etch gas may comprise between approximately 0.01% v/v to approximately 99.99% v/v of the mixture introduced into the chamber.

The alternating layers of the first etching layer and the second etching layer and the activated hydrofluorocarbon etching gas react to form volatile by-products that are removed from the reaction chamber. The a-C mask, antireflective coating, and photoresist layer are less reactive with the activated hydrofluorocarbon etching gas.

The temperature and the pressure within the reaction chamber are held at conditions suitable for the alternating layers, such as the silicon-containing film, to react with the activated hydrofluorocarbon etching gas. For instance, the pressure in the chamber may be held between approximately 0.1 mTorr and approximately 1000 Torr, preferably between approximately 1 mTorr and approximately 10 Torr, more preferably between approximately 10 mTorr and approximately 1 Torr, and more preferably between approximately 10 mTorr and approximately 100 mTorr. Likewise, the substrate temperature in the chamber may range between approximately $-196°$ C. to approximately $500°$ C., preferably between approximately $-120°$ C. to approximately $300°$ C., more preferably between approximately $-100°$ C. to approximately $50°$ C.; and more preferably between approximately −10° C. to approximately 40° C. Chamber wall temperatures may range from approximately −196° C. to approximately 300° C.

The reactions between the alternating layers and the activated hydrofluorocarbon etching gas result in anisotropic removal of the alternating layers from the substrate. Atoms of nitrogen, oxygen, and/or carbon may also be present in the alternating layers. The removal is due to a physical sputtering of alternating layers from plasma ions (accelerated by the plasma) and/or by chemical reaction of plasma species to convert Si to volatile species, such as $SiF_x$, wherein x ranges from 1-4.

The plasma activated disclosed hydrofluorocarbon etching gases preferably exhibit high to infinite selectivity toward the mask layer and low to no selectivity toward the alternating layers of the first etching layer and the second etching layer. The plasma activated disclosed hydrofluorocarbon etching gases result in a vertical etch profile with little to no bowing or roughness and high aspect ratio, which is important for 3D NAND applications. Additionally, the plasma activated hydrofluorocarbon etching gas deposits polymer on sidewall to minimize feature profile deformation. As shown in the examples that follow, the plasma activated hydrofluorocarbon etching gas may selectively etch SiO and/or SiN from mask layers, such as a-C and photoresist; or from metal contact layers, such as Cu. The selectivity of etching SiO versus SiN by the plasma activated hydrofluorocarbon etching gas may be ranged from 1:2 to 2:1, preferably around 1:1, resulting in an etching break through both SiO and SiN layers.

The disclosed etch processes produce contact holes, channel holes, staircase contacts, capacitor holes, etc., such as in 3D NAND flash memory, such as silicon-containing films. The resulting aperture may have an aspect ratio ranging from approximately 1:1 to approximately 200:1 and a diameter of approximately ranging from 5 nm to 200 nm. For example, one of ordinary skill in the art will recognize that a channel hole etch produces apertures in the silicon-containing films having an aspect ratio greater than 60:1, and a diameter as less as 40 nm.

EXAMPLES

The following non-limiting examples are provided to further illustrate embodiments of the invention. However, the examples are not intended to be all inclusive and are not intended to limit the scope of the inventions described herein.

In the following examples, the etch performance of 1,1,1,3,3,3-hexafluoropropane ($C_3H_2F_6$), 1,1,2,2,3,3-hexafluoropropane (iso-$C_3H_2F_6$), 1,1,1,2,3,3,3-heptafluoropropane ($C_3HF_7$), and 1,1,1,2,2,3,3-heptafluoropropane (iso-$C_3HF_7$) etching gases to $SiO_2$, SiN, a-C and Poly-Si layers are evaluated. The results show that $C_3H_2F_6$, iso-$C_3H_2F_6$, $C_3HF_7$, and iso-$C_3HF_7$ etching gases offer etching $SiO_2$ and SiN in a single etching process, offer sidewall protection with polymer deposition and offer high aspect ratio straight vertical etch profile with little to no bowing. As a result, $C_3H_2F_6$, iso-$C_3H_2F_6$, $C_3HF_7$, and iso-$C_3HF_7$ may be used for etching structures for NAND flash memory or ONON staircase etch. In addition, because $C_3H_2F_6$, iso-$C_3H_2F_6$, $C_3HF_7$, and iso-$C_3HF_7$ etching compounds provide polymer formation, the process maintains mask morphology and minimum sidewall deformation.

The following testing was performed using the Lam 4520 XLE advanced dielectric etch system (150 mm dual frequency capacitively coupled plasma etcher).

Figure 2:
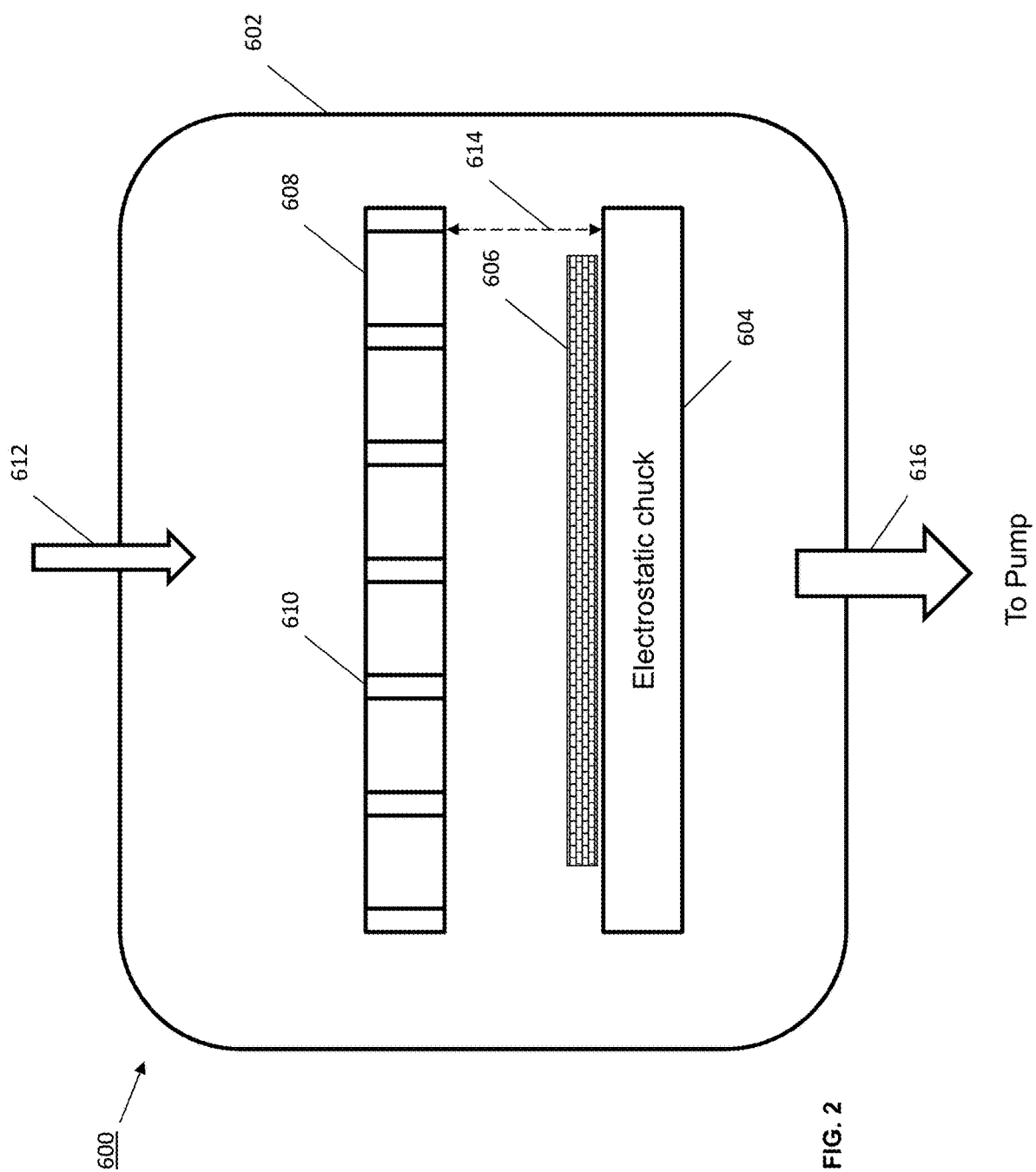
FIG. 2 is an exemplary cross-sectional side view of exemplary reactor system applied in deposition and etching tests.

FIG. 2 is an exemplary cross-sectional side view of exemplary reactor system applied in deposition and etching tests. As shown, reactor 600 includes a reactor chamber 602. A wafer 606 attached on the top of a bottom electrode 604 is placed in the bottom portion of the reactor chamber 602, and a silicon top electrode showerhead 608 is placed on the top portion of the reactor chamber 602. The bottom electrode 604 may be an electrostatic chuck having bias power applied thereto. For example, 2 MHz RF bias power is applied to the bottom electrode 604. The wafer 606 may have multi layers that need to be etched. The silicon top electrode showerhead 608 has a plurality of holes 610 through which the gases pass. The gases may be introduced into the reactor chamber 602 through gas inlet 612 and then pass through holes 610 in the showerhead 608 for uniform gas distribution. Source power may be applied to the silicon top electrode showerhead 608. For example, 27 MHz RF source power may be applied to the silicon top electrode showerhead 608. Between the silicon top electrode showerhead 608 and the bottom electrode 604 is the plasma region. Numeral 614 shows gap distance (dashed double arrows) of the silicon top electrode showerhead 608 and the bottom electrode 604. For example, a gap distance of 1.35 cm may be selected for etching tests. The gases passing through the holes 610 in the showerhead 608 are ionized in the plasma region and then perform etching on the wafer 606. The gases are removed by pumping the gases out of the reactor chamber 602 from outlet 616.

Etching tests in the following Examples 1-4 were performed on four 2×2 $cm^2$ coupons having four different substrate materials including $SiO_2$, SiN, p-Si, and a-C. The coupons were placed on 150 mm diameter carrier wafer and held in contact by thermal joint compound obtained from Wakefield Solution Inc. Alternatively, carbon tape could be used to stick coupons on carrier wafer. The etching tests were performed at 30 mTorr, source power of 750 W (27 MHz), and bias power of 1500 W (2 MHz). The flow rate of etching gas was 7.5 sccm; the flow rate of Ar was 250 sccm; and the flow rate of $O_2$ was varied in few sccm (e.g., 1, 5, 10 and 15 sccm) increments to find crossover between etch/polymer deposition. The etching time was 60 seconds.

Example 1

Figure 3:
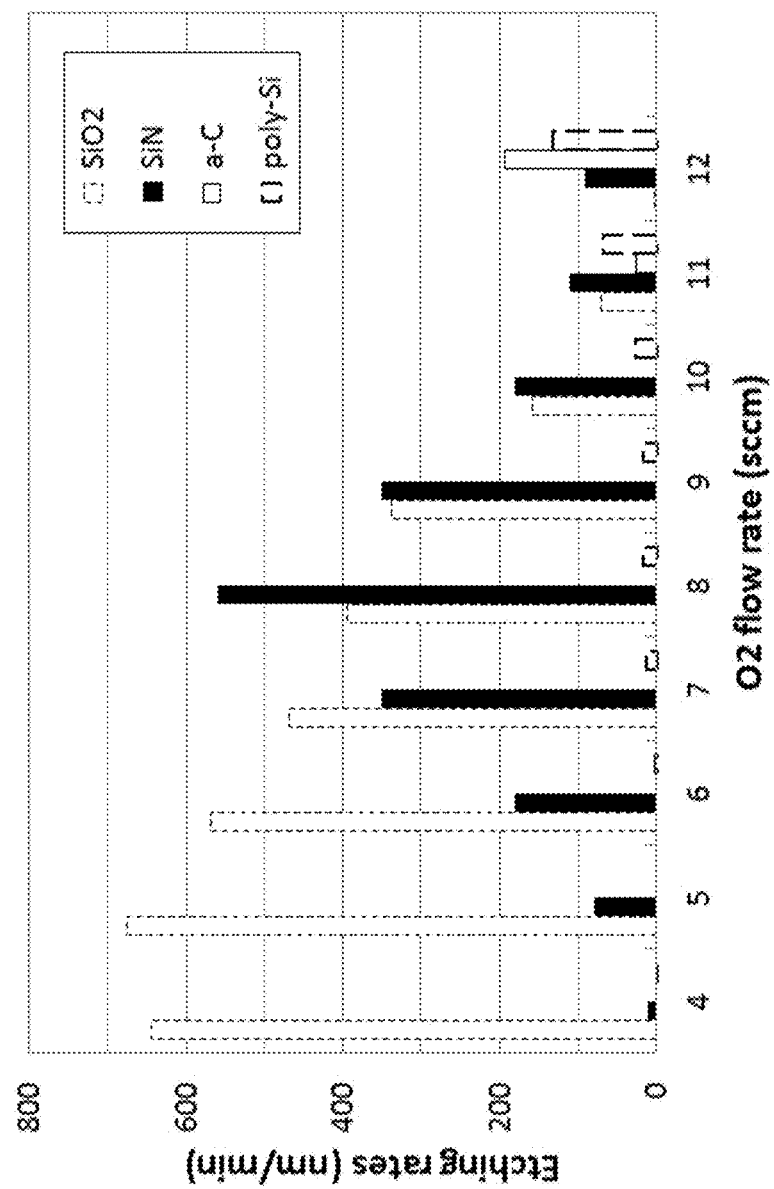
FIG. 3 is a graph demonstrating etch rates of $SiO_2$, SiN, a-C, Poly-Si versus oxygen flow rate using $C_3H_2F_6$ as etching gas.

FIG. 3 is a graph demonstrating etch rates of $SiO_2$, SiN, a-C, Poly-Si versus oxygen flow rate using $C_3H_2F_6$ ($CF_3$—$CH_2$—$CF_3$) as etching gas on a planar wafer. As shown, the etch rate of $SiO_2$ is initially high and then has a maximum value with $O_2$ flow rate of 5 sccm and then gradually reduced as $O_2$ flow rate grows. The maximum SiN etch rate of SiN occurs with $O_2$ flow at 8 sccm. Note that, when $O_2$ flow rate is in the range from 7 to 10 sccm, the etch rate of $SiO_2$ and the etch rate of SiN are high and nearly the same, whereas the etch rate of a-C and the etch rate of Poly-Si are very low and much lower than those of $SiO_2$ and SiN. This means that at $O_2$ flow rate from 7 to 10 sccm, the etching gas $C_3H_2F_6$ ($CF_3$—$CH_2$—$CF_3$) etches through $SiO_2$ and SiN layers without selectivity and selectively etches $SiO_2$ and SiN layers from a-C layer and p-Si layer.

Figure 4:
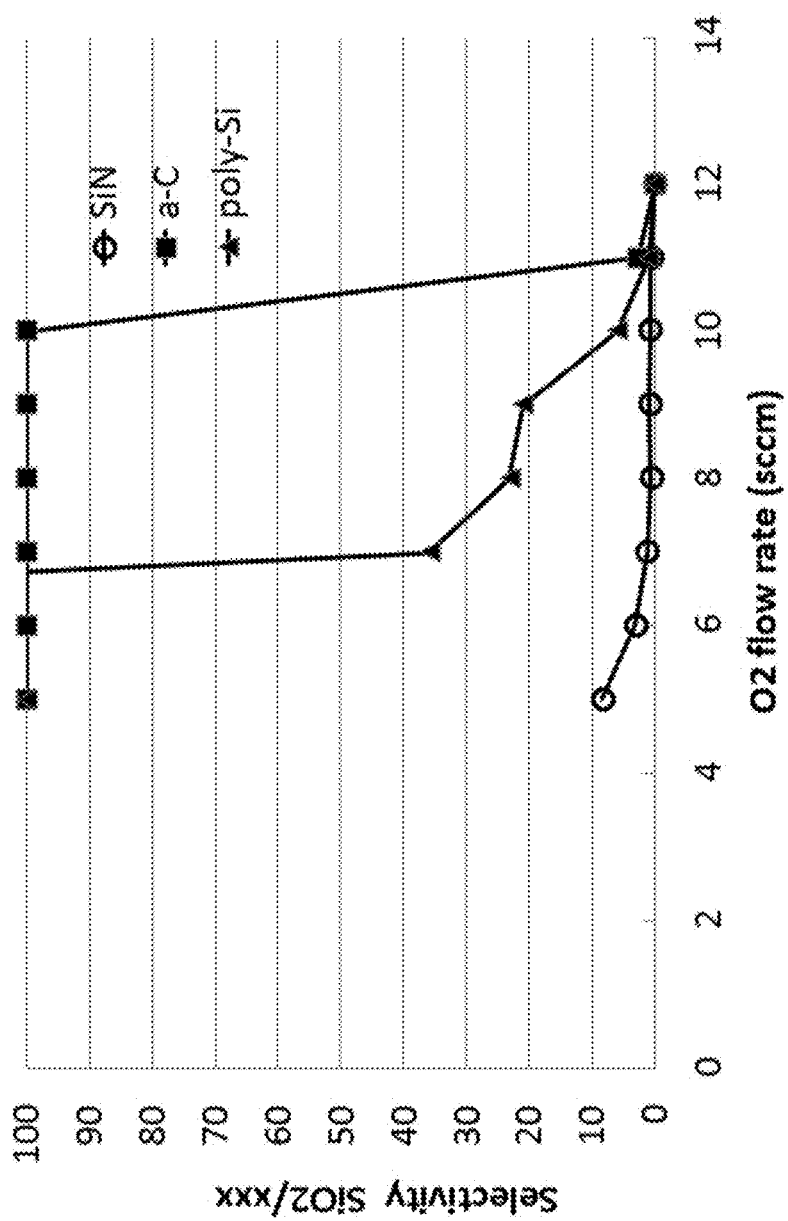
FIG. 4 is a graph demonstrating selectivity of $SiO_2$ to SiN, a-C or Poly-Si versus oxygen flow rate using $C_3H_2F_6$ as etching gas.

FIG. 4 is a graph demonstrating selectivity of $SiO_2$ to SiN, a-C or poly-Si versus oxygen flow rate using $C_3H_2F_6$ as etching gas. As shown, the selectivity of $SiO_2$ to SiN is lower than 5:1 but larger than 1:1 when $O_2$ flow rate is 6 sccm. The selectivity of $SiO_2$ to SiN is approximately 1 when $O_2$ flow rate ranges from 7 to 12 sccm. Thus, in this range, etching $SiO_2$ and etching SiN are not selective. $C_3H_2F_6$ etches both SiO and SiN layers with $O_2$ flow rate ranging from 7 to 12 sccm. Whereas, the selectivity of $SiO_2$ to a-C is infinite (100) with $O_2$ flow rate ranging from 5 to 11 sccm and then sharply decreases to almost less than 5 with $O_2$ flow rate at 11 sccm and then to 0 with $O_2$ flow rate at 12 sccm. The selectivity of $SiO_2$ to Poly-Si is infinite (100) with $O_2$ flow rate ranging from 5 to 7 sccm and sharply decreases to about 35 with $O_2$ flow rate at 7 sccm and then gradually decreases down to 0 with $O_2$ flow rate between 7 to 12 sccm. Thus, at $O_2$ flow rate ranging from 7 to 10 sccm, $C_3H_2F_6$ selectively etches $SiO_2$ and SiN layers from a-C layer and p-Si layer.

Example 2

Figure 5:
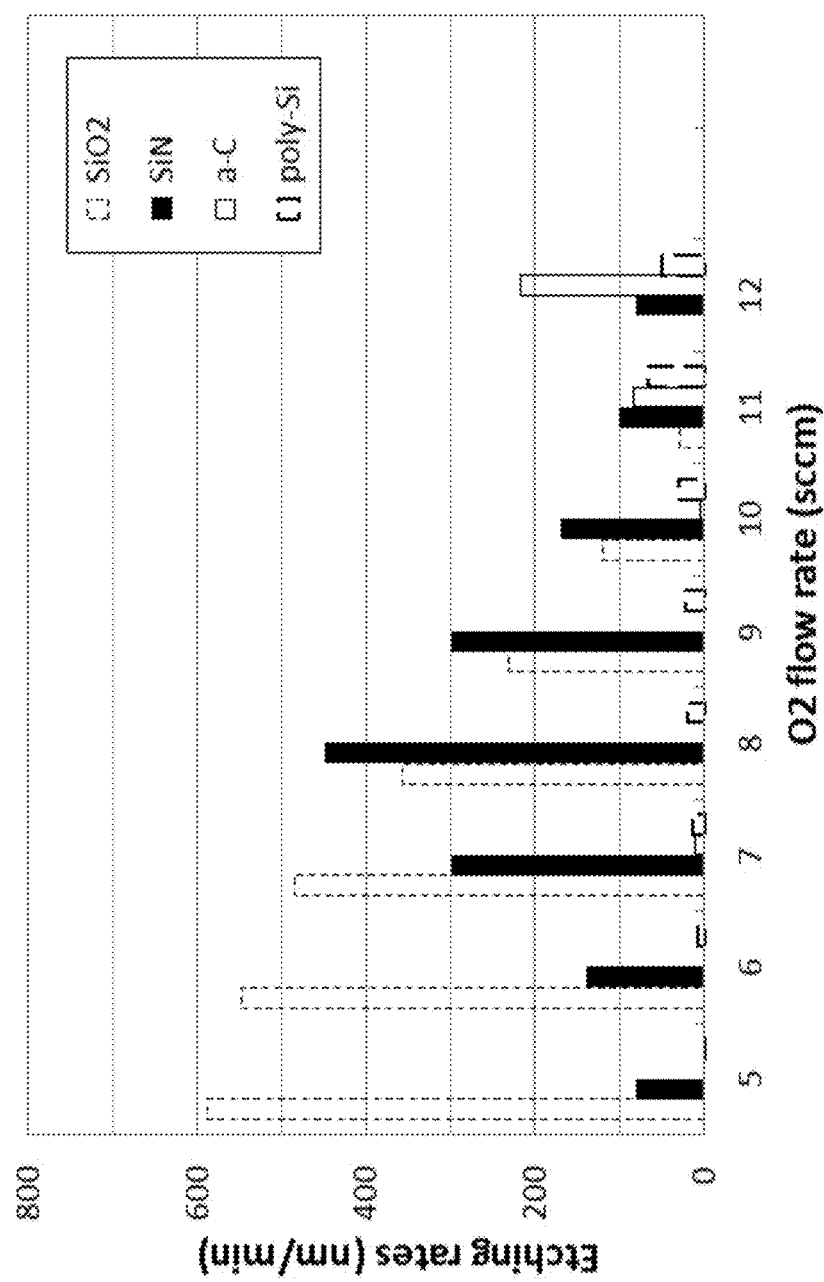
FIG. 5 is a graph demonstrating etch rates of $SiO_2$, SiN, a-C, Poly-Si versus oxygen flow rate using iso-$C_3H_2F_6$ as etching gas.
Figure 6:
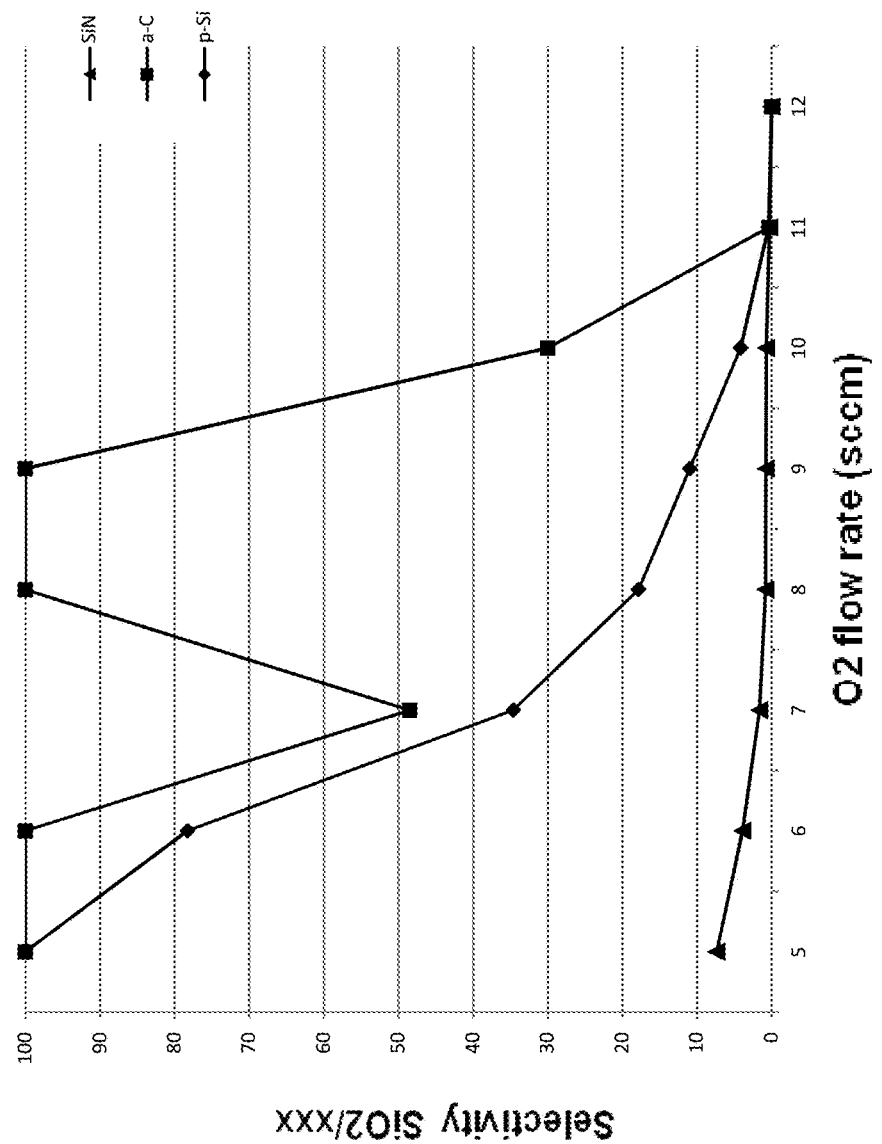
FIG. 6 is a graph demonstrating selectivity of $SiO_2$ to SiN, a-C or Poly-Si versus oxygen flow rate using iso-$C_3H_2F_6$ as etching gas.

FIG. 5 is a graph demonstrating etch rates of $SiO_2$, SiN, a-C, poly-Si versus oxygen flow rate using iso-$C_3H_2F_6$ ($CHF_2$—$CF_2$—$CHF_2$) as etching gas on a planar wafer. As shown, at $O_2$ flow rate from 7 to 10 sccm, the etching gas iso-$C_3H_2F_6$ ($CHF_2$—$CF_2$—$CHF_2$) etches through $SiO_2$ and SiN layers without selectivity and selectively etches $SiO_2$ and SiN layers from a-C layer and p-Si layer. FIG. 6 is a graph demonstrating selectivity of $SiO_2$ to SiN, a-C or Poly-Si versus oxygen flow rate using iso-$C_3H_2F_6$ as etching gas. As shown, at $O_2$ flow rate ranging from 7 to 10 sccm, iso-$C_3H_2F_6$ selectively etches $SiO_2$ and SiN layers from a-C layer and p-Si layer.

Example 3

Figure 7:
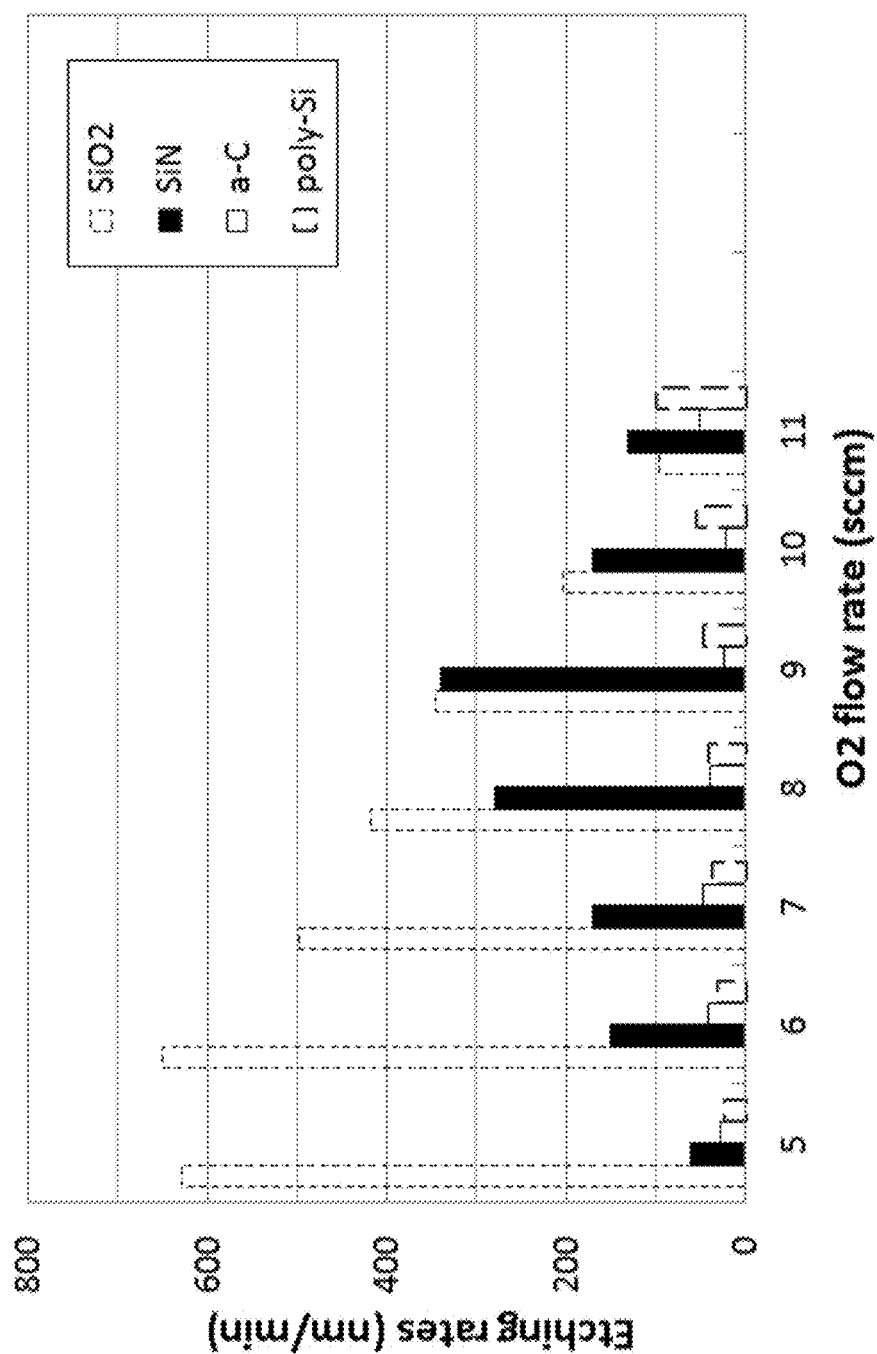
FIG. 7 is a graph demonstrating the etch rate of $SiO_2$, SiN, a-C, Poly-Si versus oxygen flow rate using $C_3HF_7$ as etching gas.
Figure 8:
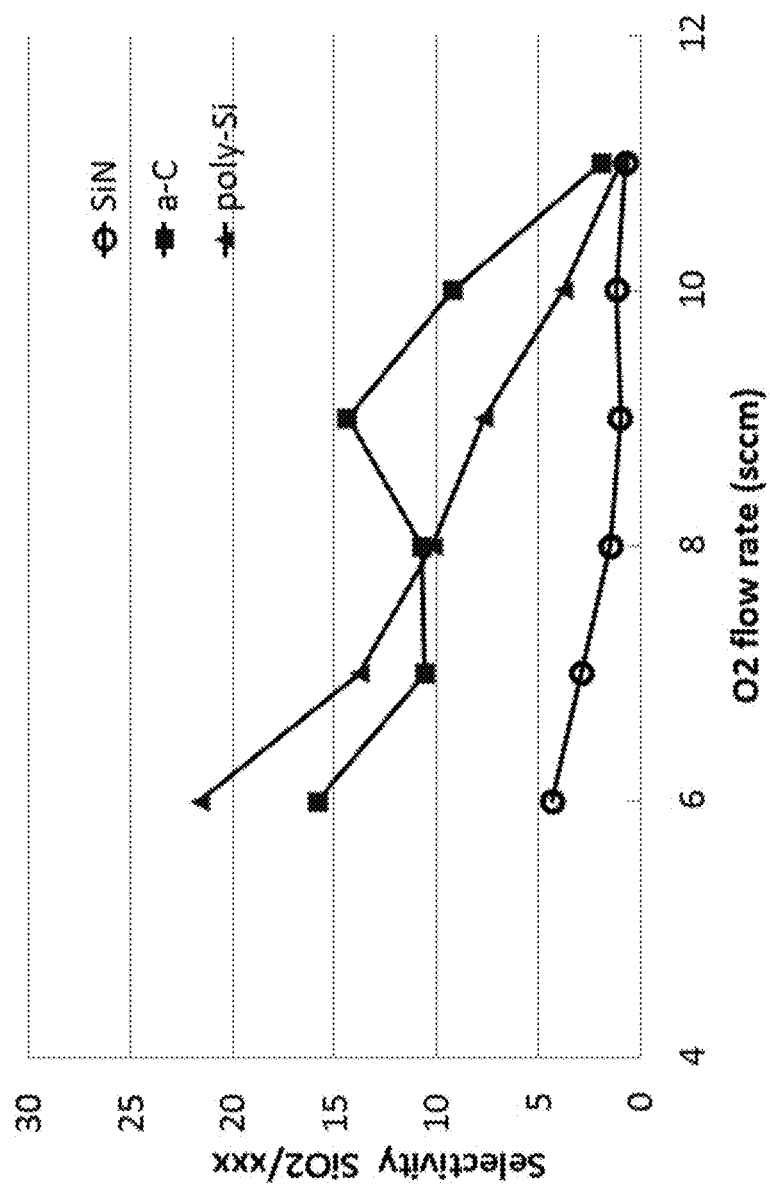
FIG. 8 is a graph demonstrating selectivity of $SiO_2$ to SiN, a-C or Poly-Si versus oxygen flow rate using $C_3HF_7$ as etching gas.

FIG. 7 is a graph demonstrating the etch rate of $SiO_2$, SiN, a-C, poly-Si versus oxygen flow rate using $C_3HF_7$ ($CF_3$—$CHF$—$CF_3$) as etching gas on a planar wafer. As shown, at $O_2$ flow rate from 8 to 11 sccm, the etching gas $C_3HF_7$ ($CF_3$—$CHF$—$CF_3$) etches through $SiO_2$ and SiN layers without selectivity but selectively etches $SiO_2$ and SiN layers from a-C layer and p-Si layer. FIG. 8 is a graph demonstrating selectivity of $SiO_2$ to SiN, a-C or Poly-Si versus oxygen flow rate using $C_3HF_7$ as etching gas. As shown, at $O_2$ flow rate ranging from 8 to 11 sccm $C_3HF_7$ selectively etches $SiO_2$ and SiN layers from a-C layer and p-Si layer.

Example 4

Figure 9:
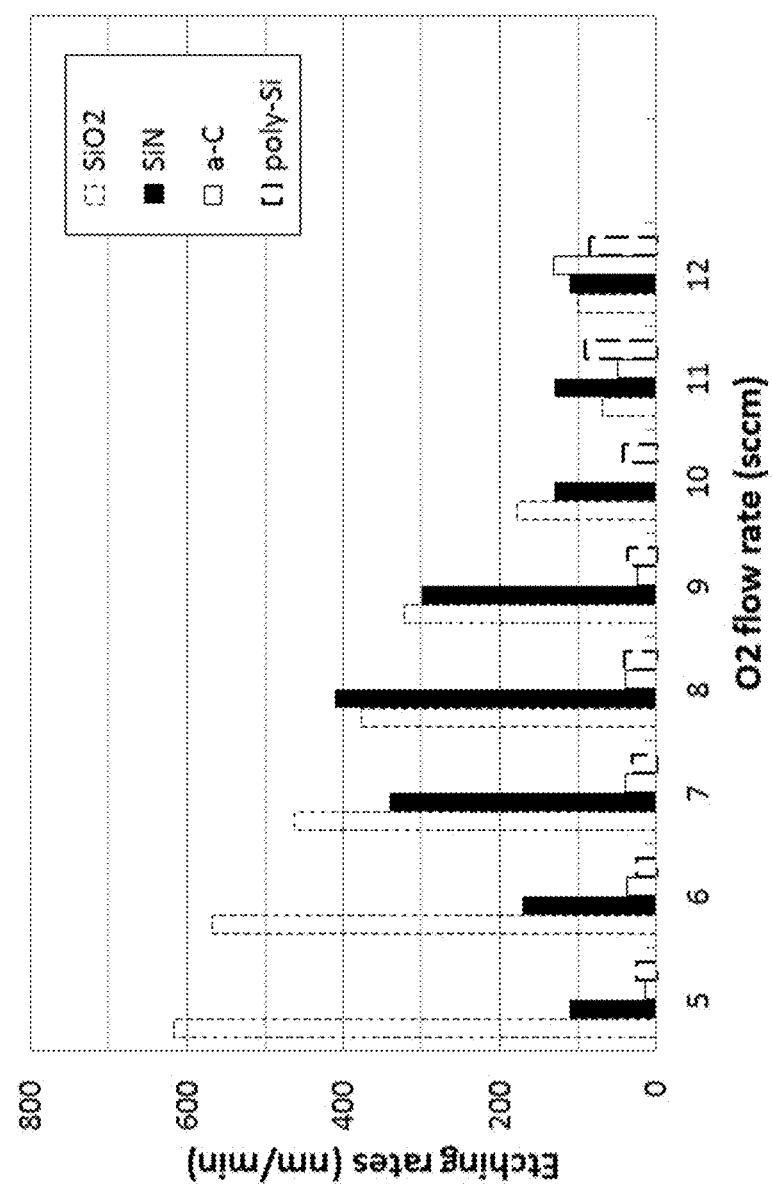
FIG. 9 is a graph demonstrating the etch rate of $SiO_2$, SiN, a-C, Poly-Si versus oxygen flow rate using iso-$C_3HF_7$ as etching gas.
Figure 10:
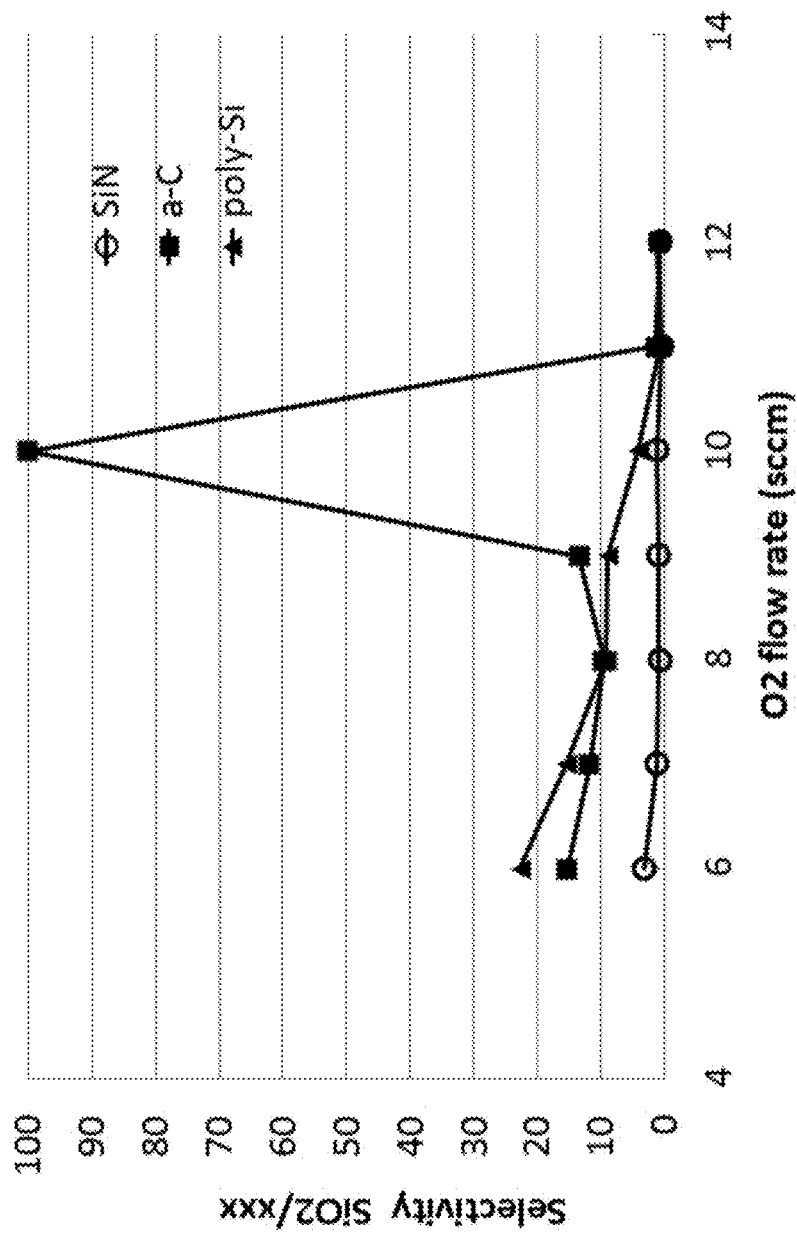
FIG. 10 is a graph demonstrating selectivity of $SiO_2$ to SiN, a-C or Poly-Si versus oxygen flow rate using iso-$C_3HF_7$ as etching gas.

FIG. 9 is a graph demonstrating the etch rate of $SiO_2$, SiN, a-C, poly-Si versus oxygen flow rate using iso-$C_3HF_7$ ($CF_3$—$CF_2$—$CHF_2$) as etching gas on a planar wafer. As shown, at $O_2$ flow rate from 7 to 10 sccm, the etching gas iso-$C_3HF_7$ ($CF_3$—$CF_2$—$CHF_2$) etches through $SiO_2$ and SiN layers without selectivity but selectively etches $SiO_2$ and SiN layers from a-C layer and p-Si layer. FIG. 10 is a graph demonstrating selectivity of $SiO_2$ to SiN, a-C or Poly-Si versus oxygen flow rate using iso-$C_3HF_7$ as etching gas. As shown, at $O_2$ flow rate around 10 sccm, iso-$C_3HF_7$ selectively etches $SiO_2$ and SiN layers from a-C layer and p-Si layer. The etching results using iso-$C_3HF_7$ ($CF_3$—$CF_2$—$CHF_2$) are different from those of $C_3HF_7$ ($CF_3$—$CHF$—$CF_3$). Thus, the choice of isomer is believed to be important.

Example 5

Figure 11:
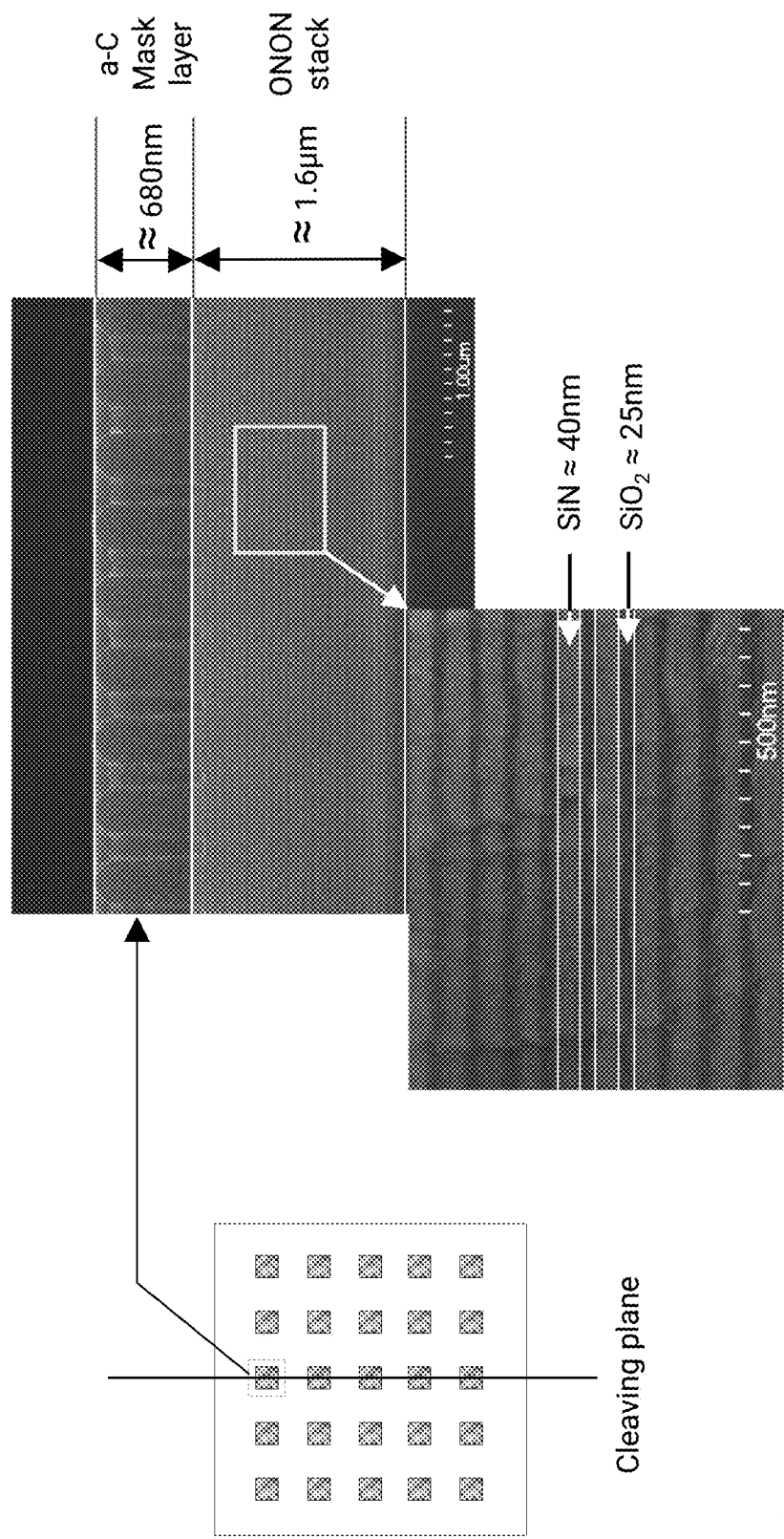
FIG. 11 is a SEM image of a patterned wafer for plasma etching.
Figure 12A:
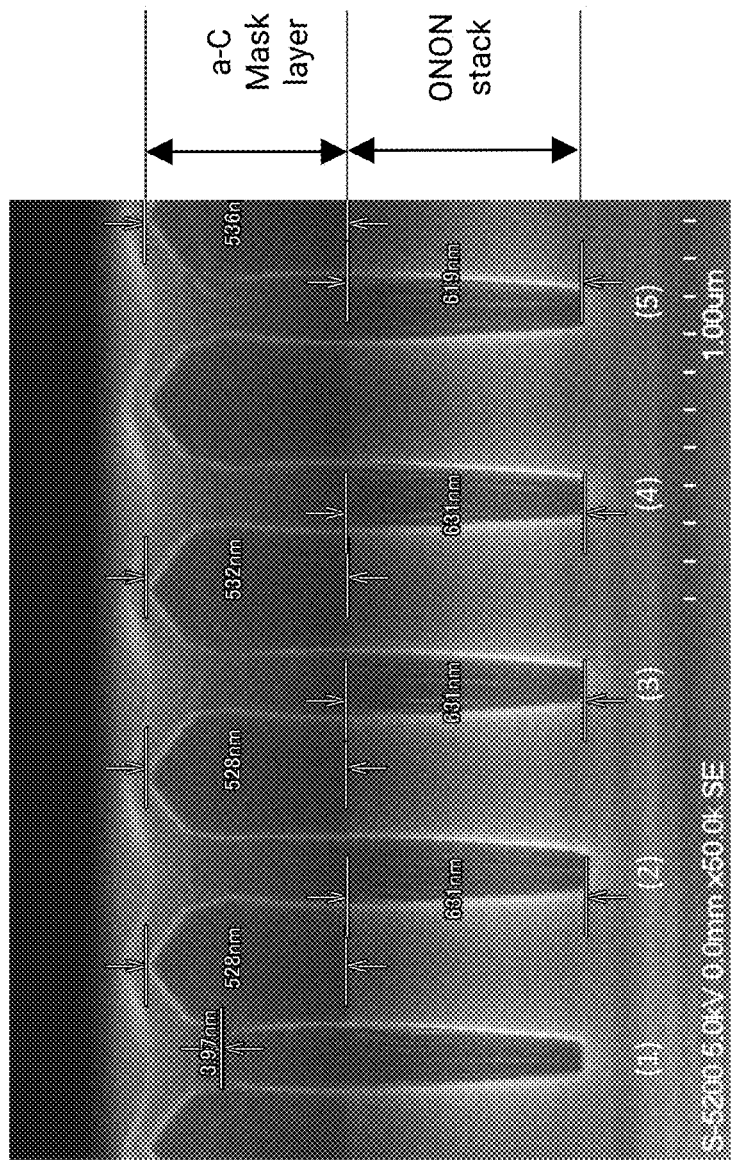
FIG. 12a is a SEM image with the depths of the etching structures marked thereon after plasma etching the patterned wafer of FIG. 11 with $C_3H_2F_6$ ($CF_3$—$CH_2$—$CF_3$) and $O_2$.
Figure 12B:
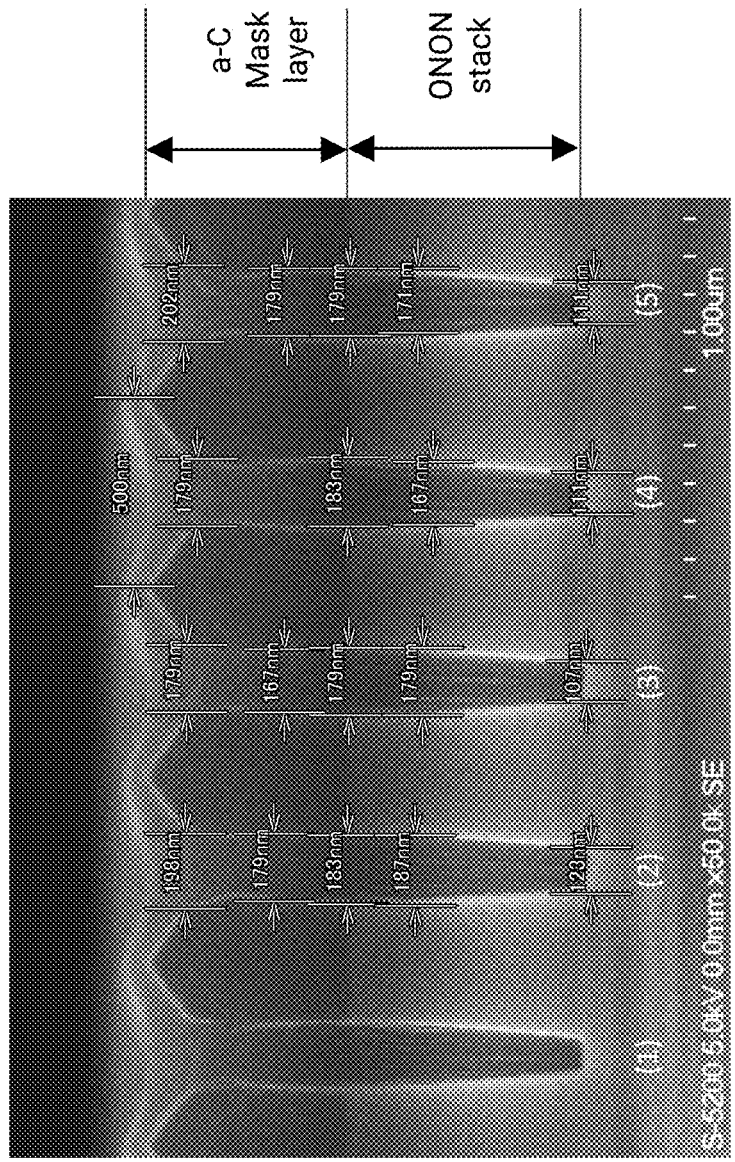
FIG. 12b is a SEM image with the widths of the etching structures marked thereon after plasma etching the patterned wafer of FIG. 11 with $C_3H_2F_6$ ($CF_3$—$CH_2$—$CF_3$) and $O_2$.

FIG. 11 is a SEM image of a patterned wafer for plasma etching. FIG. 12a-12b are SEM images after plasma etching the patterned wafer of FIG. 11 with $C_3H_2F_6$ ($CF_3$—$CH_2$—$CF_3$) and $O_2$. As shown in FIG. 11, the patterned a-C hardmask layer is about 680 nm thick with a pattern of square holes evenly distributed in the a-C hardmask layer. The ONON layer is about 1.6 um thick and has 60 alternating layers of 40 nm SiN layer and 25 nm $SiO_2$ layer (30 pairs). FIG. 12a shows apertures (1) to (5) formed by plasma etching with $C_3H_2F_6$ and $O_2$ on the ONON stack. The etching test was done at 30 mTorr, source power of 750 W (27 MHz), and bias power of 1500 W (2 MHz). The flow rate of $C_3H_2F_6$ ($CF_3$—$CH_2$—$CF_3$) was 7.5 sccm; the flow rate of $O_2$ was 10 sccm; and the flow rate of Ar was 125 sccm. The etching time was 120 seconds. The apertures (1) to (5) each have a nearly straight vertical structure with smooth sidewalls. Sidewall necking occurs on the sidewall of the a-C mask pattern layer, instead of around the ONON openings. The etching stops at around 631 nm in the ONON stack, as marked on the apertures (2) to (5). The various line width data for the apertures (2) to (5), shown in FIG. 12b, are listed in Table 2. The calculated bowings and line width bias for the apertures (2) to (5) are also listed therein.

TABLE 2

| Aperture | Max Line Width (nm) | Opening Line Width (nm) | Bottom Line Width (nm) | Bowing (%) | Line Width Bias (nm) |
|---|---|---|---|---|---|
| (2) | 187 | 183 | 123 | 1 | 60 |
| (3) | 179 | 179 | 107 | 0 | 72 |
| (4) | 167 | 183 | 111 | N/A | 72 |
| (5) | 171 | 179 | 111 | N/A | 68 |

The results show only aperture (2) has 1% bowing which is nearly zero. Consequently, the etched apertures using $C_3H_2F_6$ ($CF_3$—$CH_2$—$CF_3$) and $O_2$ have little to no bowing and good sidewall protection.

In summary, the evaluation of the dry etching of low-k films with the disclosed hydrofluorocarbon etching gases shows that the disclosed hydrofluorocarbon etching gases provide etching through SiN and $SiO_2$ layers in a single etching process without selectivity. The disclosed hydrofluorocarbon etching gases also provide selectively etching the SiN and $SiO_2$ layers from a-C mask layer. Simultaneously, during the etching process, the disclosed hydrofluorocarbon etching gases form a layer of polymer on the sidewall of the etch structure to protect the etch profile. The disclosed hydrofluorocarbon etching gases provide a high aspect ratio etching profile with little to no bowing and good sidewall protection.

While embodiments of this invention have been shown and described, modifications thereof may be made by one skilled in the art without departing from the spirit or teaching of this invention. The embodiments described herein are exemplary only and not limiting. Many variations and modifications of the compound and method are possible and within the scope of the invention. Accordingly, the scope of protection is not limited to the embodiments described herein, but is only limited by the claims which follow, the scope of which shall include all equivalents of the subject matter of the claims.

What is claimed is:
1. A method for fabricating a 3D NAND flash memory having alternating layers of a first etching layer and a second etching layer on a substrate and a hardmask layer on the alternating layers, the method comprising the steps of:
   forming a hardmask pattern on the hardmask layer; and
   using the hardmask pattern to form apertures having a sidewall bowing less than approximately 5% in the alternating layers by selectively plasma etching the alternating layers of the first etching layer and the second etching layer versus the hardmask layer using an etching gas consisting of a hydrofluorocarbon etching gas selected from the group consisting of 1,1,1,3,3,3-hexafluoropropane ($C_3H_2F_6$), 1,1,2,2,3,3-hexafluoropropane (iso-$C_3H_2F_6$), 1,1,1,2,3,3,3-heptafluoropropane ($C_3HF_7$), 1,1,1,2,2,3,3-heptafluoropropane (iso-$C_3HF_7$), and combinations thereof, a fluorocarbon etching gas containing hydrogen or iodine selected from the group consisting of c$C_4F_8$, $C_4F_8$, $C_4F_6$, $C_5F_8$, $CF_4$, $CH_3F$, $CF_3H$, $CH_2F_2$, $CF_3I$, $C_2F_3I$, $C_2F_5I$ and combinations thereof, an oxygen-containing gas and an inert gas, wherein the first etching layer comprises a material different from that of the second etching layer, wherein the hydrofluorocarbon etching gases plasma etch the first etching layer versus the second etching layer with a selectivity between approximately 1:2 to approximately 2:1, and wherein the apertures have an aspect ratio within a range from larger than 20:1 to approximately 200:1.

2. The method of claim 1, wherein the alternating layers comprises a layer of silicon oxide, silicon nitride, SiOCN, SiON, $Si_aO_bH_cC_dN_e$, where a>0; b, c, d and e≥0, or combinations thereof.

3. The method of claim 1, wherein the first etching layer comprises a silicon oxide layer and the second etching layer comprises a silicon nitride layer, and vice versa.

4. The method of claim 1, wherein the hardmask layer is selected from the group consisting of CVD or spin on deposited layer of amorphous carbon or doped carbon, silicon-containing spin on mask, and carbon-containing spin on mask.

5. The method of claim 1, wherein the oxygen-containing gas is selected from the group consisting of $O_2$, $O_3$, CO, $CO_2$, NO, $NO_2$, $N_2O$, $SO_2$, COS, $H_2O$ and combination thereof.

6. The method of claim 5, wherein the hydrofluorocarbon etching gas is 1,1,2,2,3,3-hexafluoropropane (iso-$C_3H_2F_6$).

7. The method of claim 5, wherein the hydrofluorocarbon etching gas is 1,1,1,2,3,3,3-Heptafluoropropane ($C_3HF_7$).

8. The method of claim 5, wherein the hydrofluorocarbon etching gas is 1,1,1,2,2,3,3-heptafluoropropane (iso-$C_3HF_7$).

9. The method of claim 1, wherein the hydrofluorocarbon etching gases plasma etch the alternating layers of the first etching layer and the second etching layer versus the hardmask layer with an infinite selectivity.

10. The method of claim 1, wherein the hydrofluorocarbon etching gases plasma etch the first etching layer versus the second etching layer with a selectivity of approximately 1:1.

11. The method of claim 1, further comprising the step of heating the hydrofluorocarbon etching gas to maintain a predetermined flow rate of the hydrofluorocarbon etching gas for plasma etching and to avoid condensation.

12. The method of claim 5, wherein the hydrofluorocarbon etching gas is 1,1,1,3,3,3-hexafluoropropane ($C_3H_2F_6$).

13. A method for fabricating a 3D NAND flash memory having alternating layers of a first etching layer and a second etching layer on a substrate and a hardmask layer on the alternating layers, the method comprising the steps of:

forming a hardmask pattern on the hardmask layer; and using the hardmask pattern to form apertures having a sidewall bowing less than approximately 5% in the alternating layers by selectively plasma etching the alternating layers of the first etching layer and the second etching layer versus the hardmask layer using an etching gas consisting of a first hydrofluorocarbon etching gas selected from the group consisting of 1,1,1,3,3,3-hexafluoropropane ($C_3H_2F_6$), 1,1,2,2,3,3-hexafluoropropane (iso-$C_3H_2F_6$), 1,1,1,2,3,3,3-heptafluoropropane ($C_3HF_7$), 1,1,1,2,2,3,3-heptafluoropropane (iso-$C_3HF_7$), and combinations thereof, a second fluorocarbon or hydrofluorocarbon etching gas selected from the group consisting of c$C_4F_8$, $C_4F_8$, $C_4F_6$, $C_5F_8$, $CF_4$, $CH_3F$, $CF_3H$, $CH_2F_2$ and combinations thereof, an oxygen-containing gas and an inert gas, wherein the first etching layer comprises a material different from that of the second etching layer, wherein the hydrofluorocarbon etching gases plasma etch the first etching layer versus the second etching layer with a selectivity between approximately 1:2 to approximately 2:1, and wherein the apertures have an aspect ratio within a range from larger than 20:1 to approximately 200:1.

14. The method of claim 13, wherein the alternating layers comprises a layer of silicon oxide, silicon nitride, SiOCN, SiON, $Si_aO_bH_cC_dN_e$, where a>0; b, c, d and e≥0, or combinations thereof.

15. The method of claim 13, wherein the first etching layer comprises a silicon oxide layer and the second etching layer comprises a silicon nitride layer, and vice versa.

16. The method of claim 13, wherein the hardmask layer is selected from the group consisting of CVD or spin on deposited layer of amorphous carbon or doped carbon, silicon-containing spin on mask, and carbon-containing spin on mask.

17. The method of claim 13, wherein the hydrofluorocarbon etching gas is 1,1,1,3,3,3-hexafluoropropane ($C_3H_2F_6$).

18. The method of claim 13, wherein the hydrofluorocarbon etching gases plasma etch the first etching layer versus the second etching layer with a selectivity of approximately 1:1.

19. The method of claim 13, further comprising the step of heating the hydrofluorocarbon etching gas to maintain a predetermined flow rate of the hydrofluorocarbon etching gas for plasma etching and to avoid condensation.

20. The method of claim 13, wherein the oxygen-containing gas is selected from the group consisting of $O_2$, $O_3$, CO, $CO_2$, NO, $NO_2$, $N_2O$, $SO_2$, COS, $H_2O$ and combination thereof.

* * * * *